(12) United States Patent
Ahn et al.

(10) Patent No.: US 12,030,255 B2
(45) Date of Patent: Jul. 9, 2024

(54) 3D PRINTING SYSTEM FOR MANUFACTURING ARTIFICIAL BLOOD VESSEL AND METHOD FOR MANUFACTURING ARTIFICIAL BLOOD VESSEL USING SAME

(71) Applicant: T&R Biofab Co., Ltd., Siheung-si (KR)

(72) Inventors: Geun Seon Ahn, Seongnam-si (KR); Min Kyung Kim, Seongnam-si (KR); Kyung Hyun Min, Seongnam-si (KR); In Gyu Lee, Seongnam-si (KR)

(73) Assignee: T&R BIOFAB CO., LTD., Siheung-si (KR)

( * ) Notice: Subject to any disclaimer, the term of this patent is extended or adjusted under 35 U.S.C. 154(b) by 895 days.

(21) Appl. No.: 17/059,401

(22) PCT Filed: Dec. 17, 2019

(86) PCT No.: PCT/KR2019/017877
§ 371 (c)(1),
(2) Date: Nov. 27, 2020

(87) PCT Pub. No.: WO2021/107252
PCT Pub. Date: Jun. 3, 2021

(65) Prior Publication Data
US 2021/0379835 A1 Dec. 9, 2021

(30) Foreign Application Priority Data
Nov. 26, 2019 (KR) .................. 10-2019-0153497

(51) Int. Cl.
*B29C 64/40* (2017.01)
*A61F 2/06* (2013.01)
(Continued)

(52) U.S. Cl.
CPC ............... *B29C 64/40* (2017.08); *A61F 2/06* (2013.01); *B29C 64/106* (2017.08);
(Continued)

(58) Field of Classification Search
CPC ................ B29L 2031/7534; G06F 2113/10
See application file for complete search history.

(56) References Cited

U.S. PATENT DOCUMENTS

2016/0167312 A1  6/2016  Feinberg et al.
2018/0112167 A1  4/2018  Kang et al.
(Continued)

FOREIGN PATENT DOCUMENTS

CN    102149859 A    8/2011
CN    104607681 A    5/2015
(Continued)

OTHER PUBLICATIONS

International Search Report of PCT/KR2019/017877, Aug. 26, 2020.
The partial supplementary European search report of 19929182.4, Nov. 15, 2021.

*Primary Examiner* — Thaddeus B Cox
(74) *Attorney, Agent, or Firm* — STIP Law Group, LLC

(57) ABSTRACT

The present invention relates to a three-dimensional (3D) printing system for manufacturing an artificial blood vessel and a method for manufacturing an artificial blood vessel using the same, wherein a cylindrical support having a hollow 3D porous structure including a thermoplastic polymer is manufactured and vertically fixed, and a hydrogel divided into at least two sections is discharged into the support, thereby maintaining the structure and shape constantly even after printing and manufacturing an artificial blood vessel having a hollow multilayered structure. The 3D printing system for manufacturing an artificial blood vessel comprises: a rotatable support manufacturing unit which
(Continued)

forms a hollow cylindrical support having a 3D porous structure by discharging a polymer to the outer circumference thereof through a first head; a first head which forms a hollow cylindrical support having a 3D porous structure by discharging a polymer to the support manufacturing unit; a support vertically holding the hollow cylindrical support manufactured through the first head; and a second head which discharges a hydrogel, divided into at least two sections, into the cylindrical support vertically held and fixed to the support.

8 Claims, 20 Drawing Sheets

(51) Int. Cl.
  *B29C 64/106* (2017.01)
  *B29C 64/209* (2017.01)
  *B33Y 10/00* (2015.01)
  *B33Y 30/00* (2015.01)
  *B33Y 70/00* (2020.01)
  *B33Y 80/00* (2015.01)
  *A61F 2/00* (2006.01)
  *B29K 101/12* (2006.01)
  *B29K 105/00* (2006.01)
  *B29L 31/00* (2006.01)

(52) U.S. Cl.
  CPC ............ *B29C 64/209* (2017.08); *B33Y 10/00* (2014.12); *B33Y 30/00* (2014.12); *B33Y 70/00* (2014.12); *B33Y 80/00* (2014.12); *A61F 2002/0081* (2013.01); *A61F 2240/002* (2013.01); *B29K 2101/12* (2013.01); *B29K 2105/0061* (2013.01); *B29L 2031/7534* (2013.01)

(56) References Cited

U.S. PATENT DOCUMENTS

| | | |
|---|---|---|
| 2018/0207856 A1 | 7/2018 | Seriani |
| 2018/0229426 A1 | 8/2018 | Douroumis et al. |
| 2018/0369451 A1 | 12/2018 | Rapoport et al. |

FOREIGN PATENT DOCUMENTS

| | | |
|---|---|---|
| CN | 205519737 U | 8/2016 |
| CN | 106806945 A | 6/2017 |
| CN | 107296983 A | 10/2017 |
| CN | 107411844 A | 12/2017 |
| CN | 110004058 A | 7/2019 |
| CN | 110480540 A | 11/2019 |
| DE | 202014103517 01 | 1/2015 |
| DE | 202018106923 U1 | 12/2018 |
| JP | U58157465 U | 10/1983 |
| JP | 2014151524 A | 8/2014 |
| JP | 2018154049 A | 10/2018 |
| JP | 2019516577 A | 6/2019 |
| KR | 101067827 B1 | 9/2011 |
| KR | 101519922 B1 | 5/2015 |
| KR | 20160096829 A | 8/2016 |
| KR | 20170008407 A | 1/2017 |
| KR | 20170113437 A | 10/2017 |
| KR | 20180042220 A | 4/2018 |
| KR | 101863192 B1 | 6/2018 |
| KR | 20180130639 A | 12/2018 |
| KR | 102083788 A | 3/2020 |

[FIG. 1]
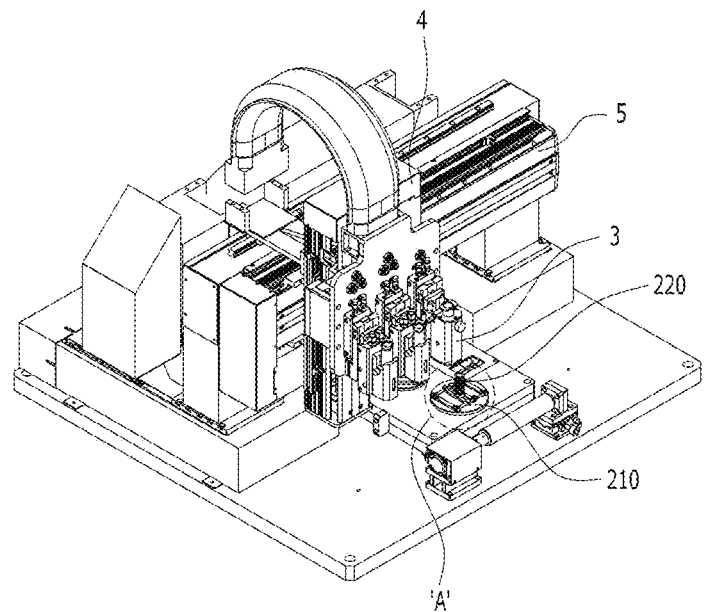
[FIG. 2]
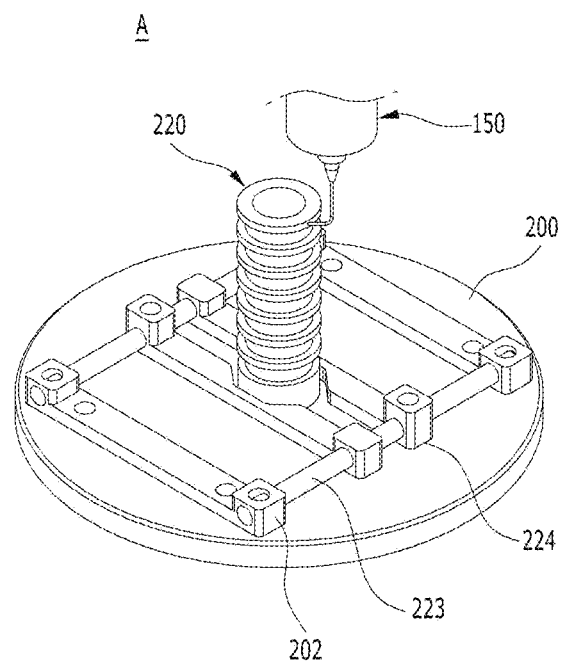

[FIG. 3]
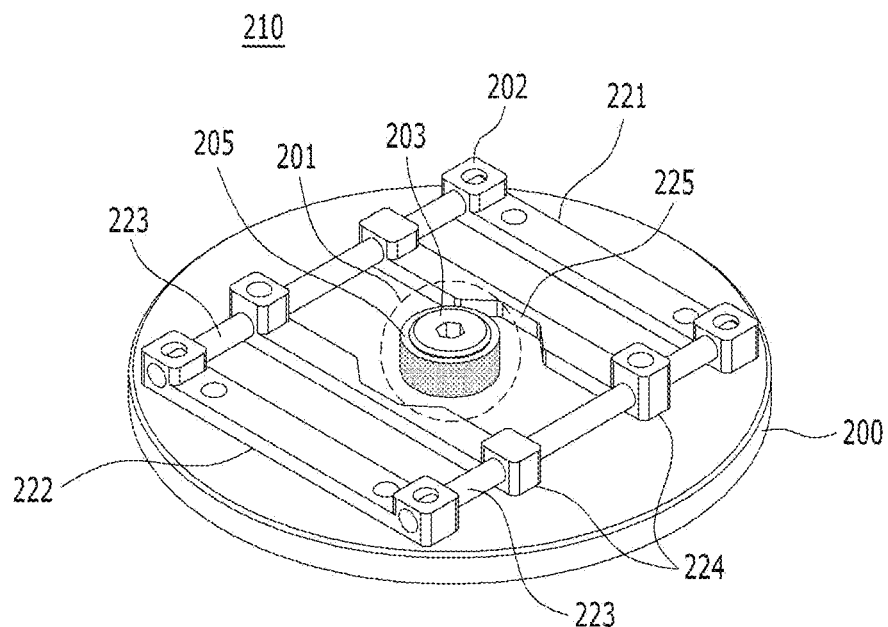
[FIG. 4]
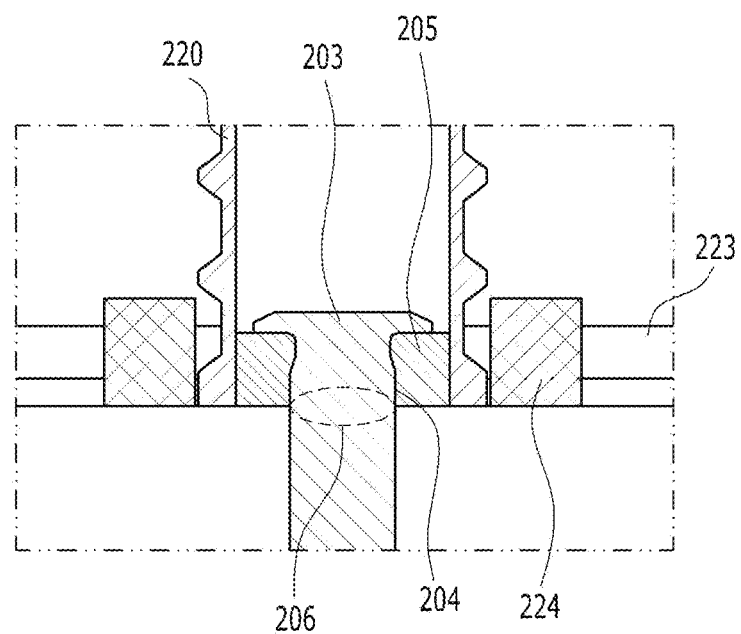

[FIG. 5a]
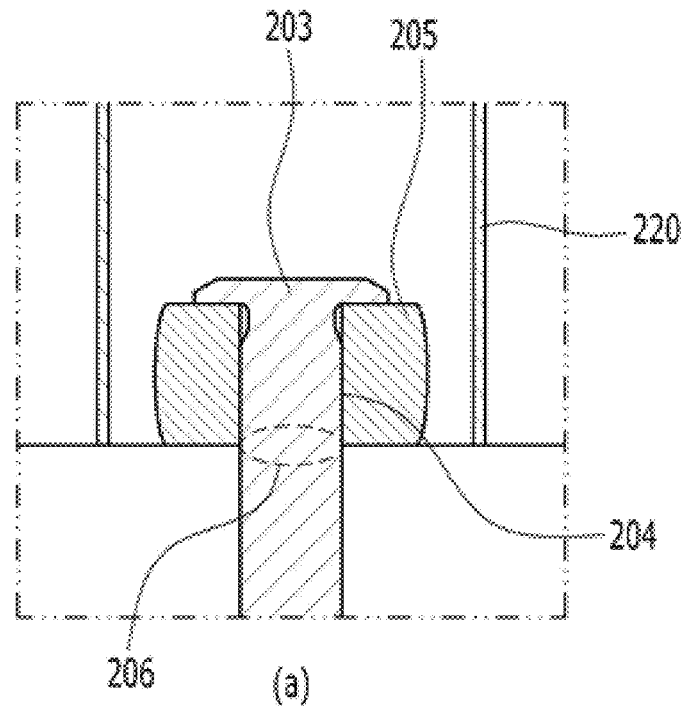
(a)
[FIG. 5b]
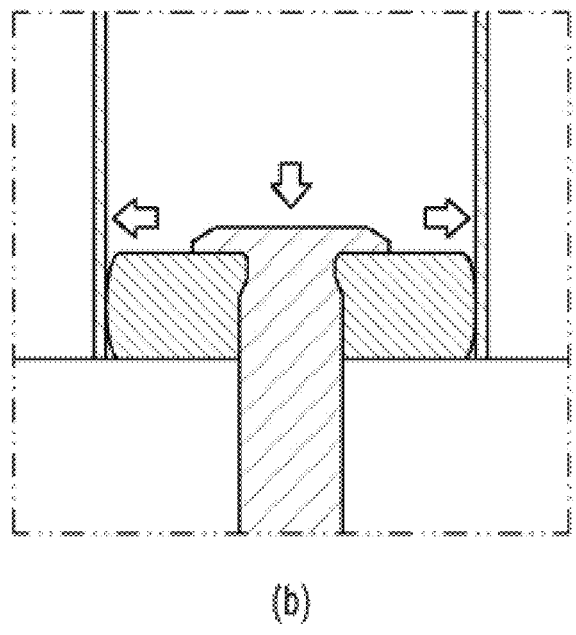
(b)

[FIG. 6a]
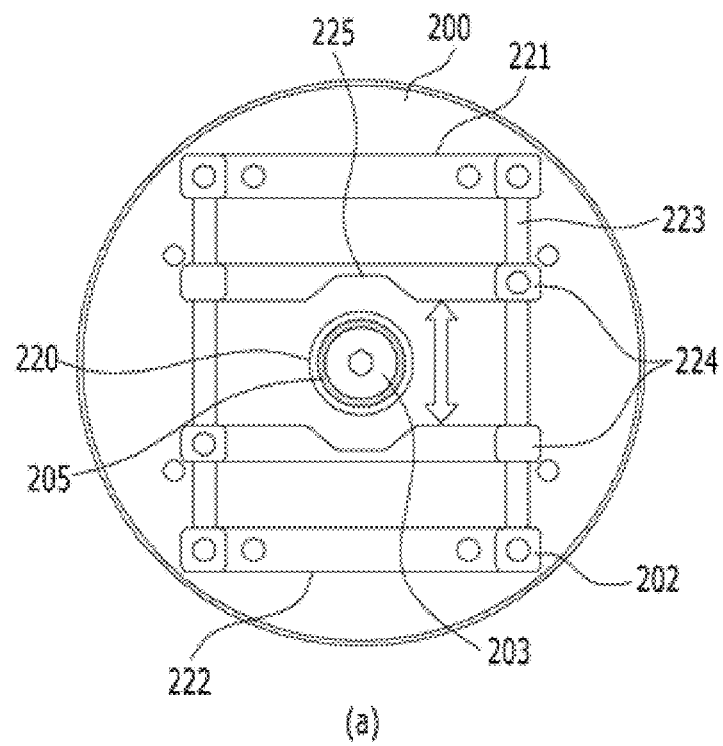
(a)
[FIG. 6b]
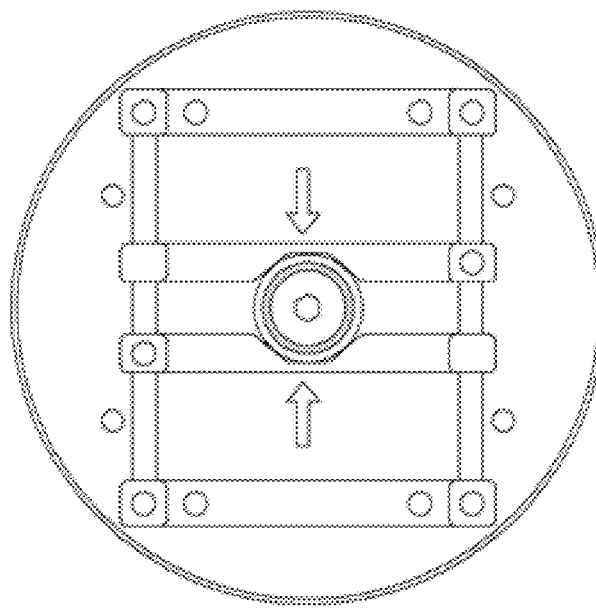
(b)

[FIG. 7]
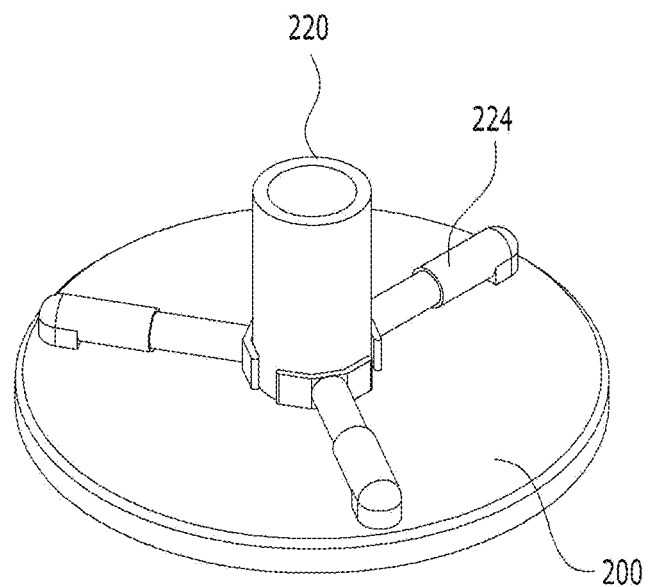
[FIG. 8]
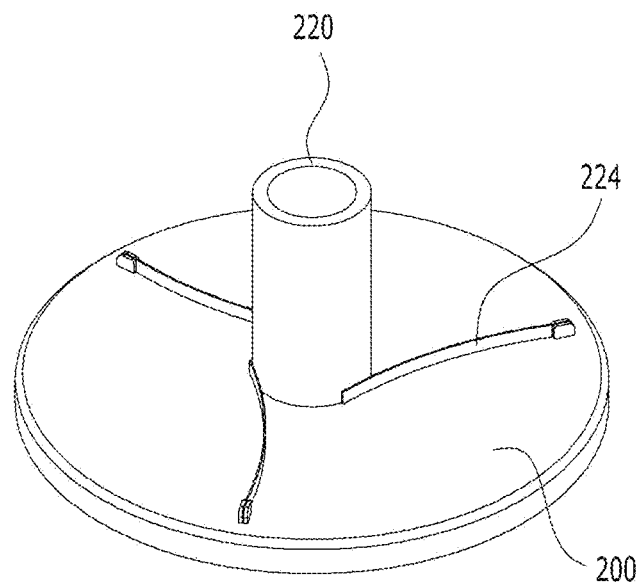

[FIG. 9]
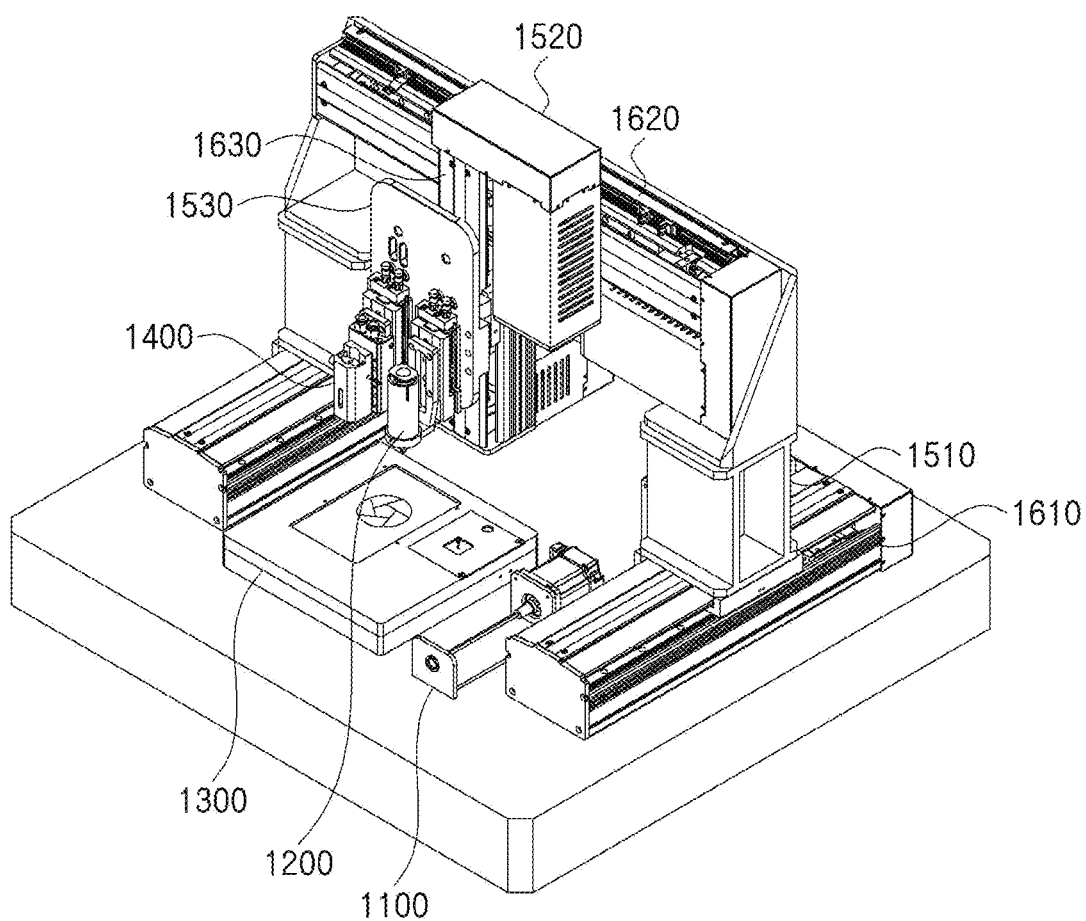

[FIG. 10]
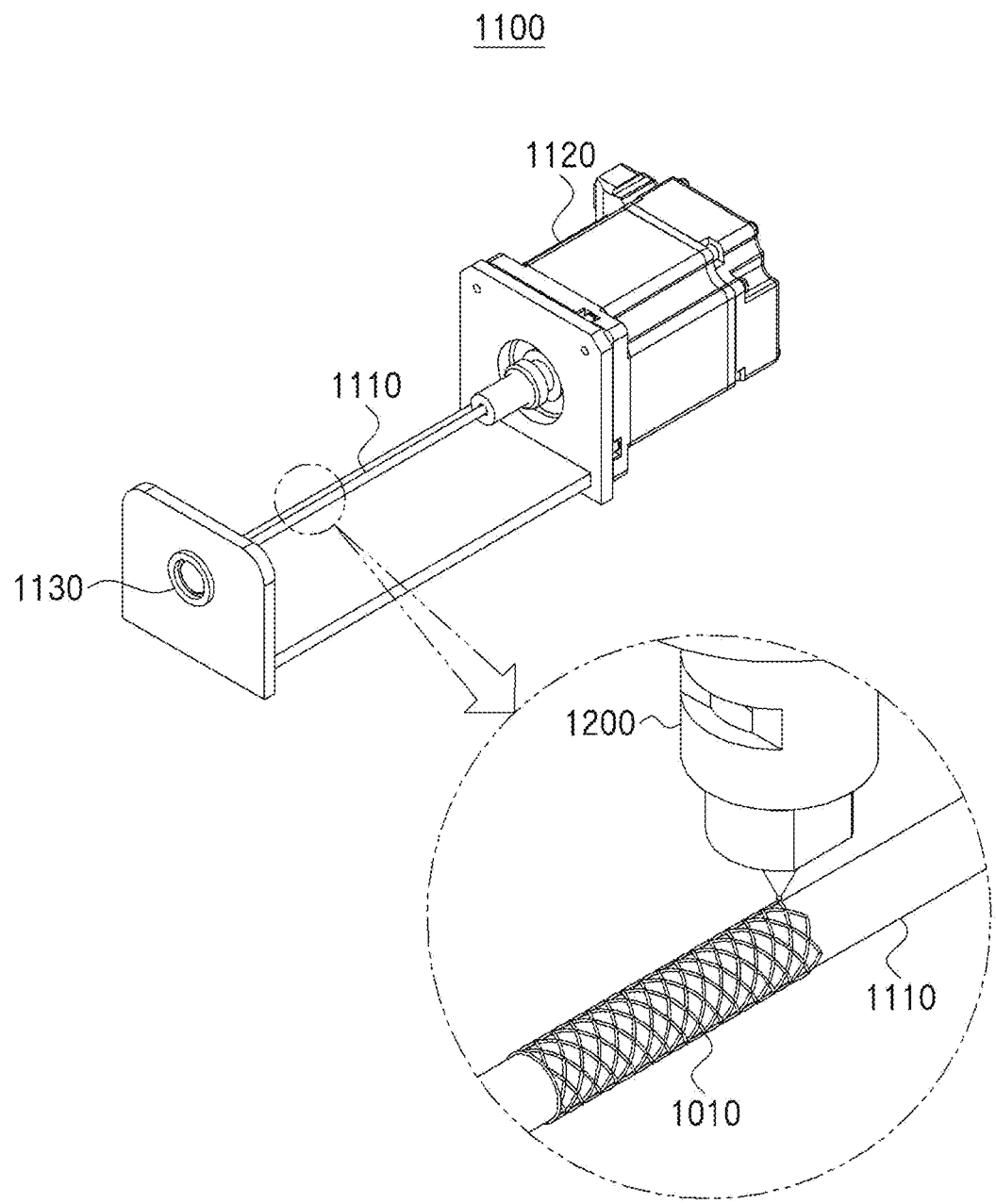

[FIG. 11]
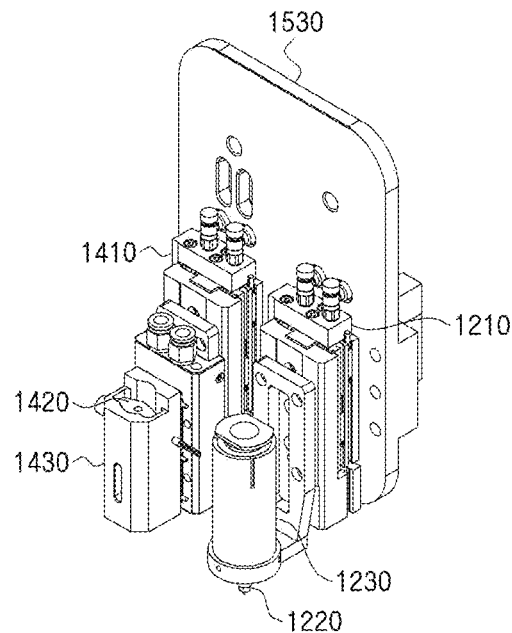
[FIG. 12]
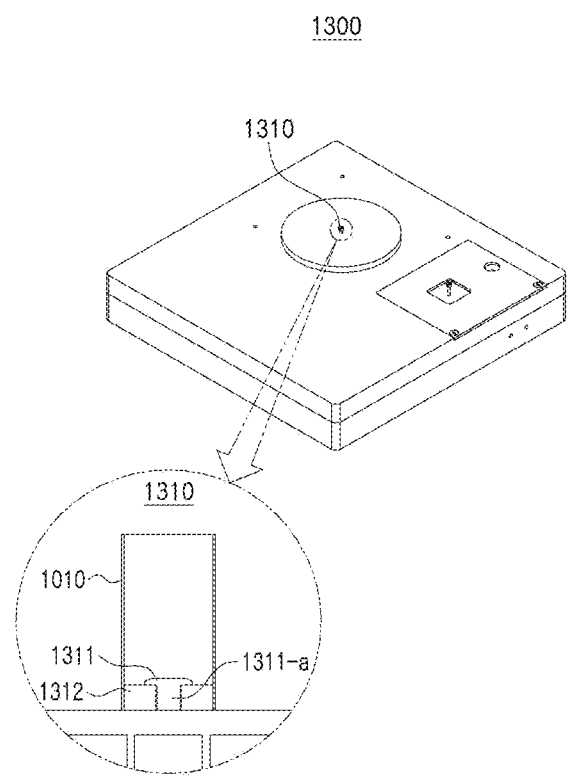

[FIG. 13]
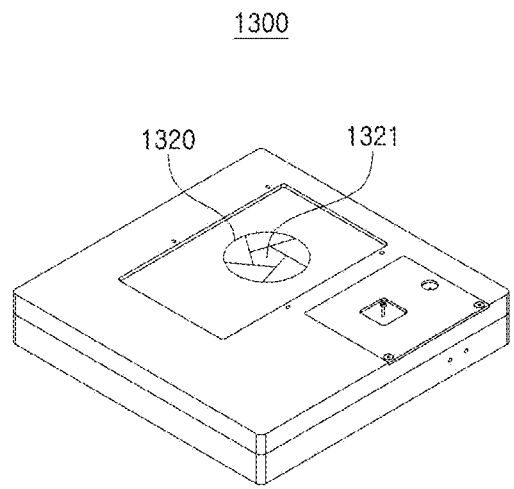
[FIG. 14]
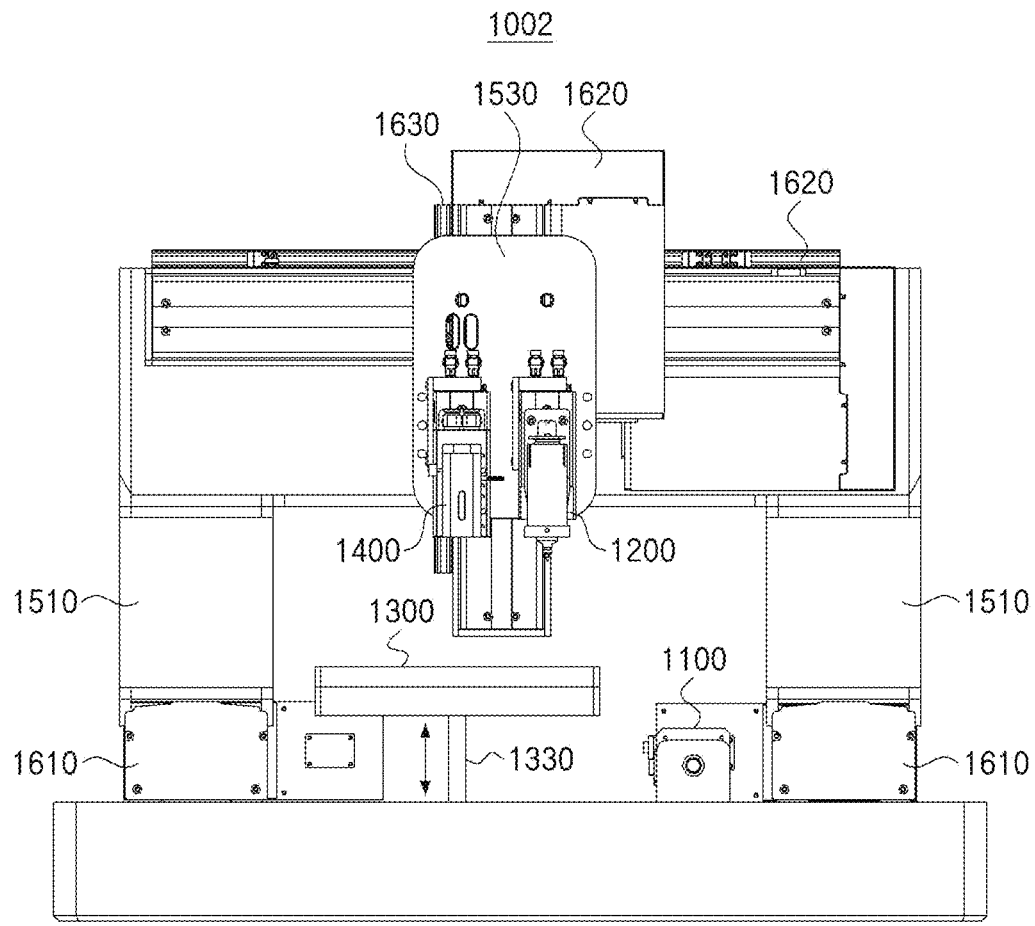

[FIG. 15]
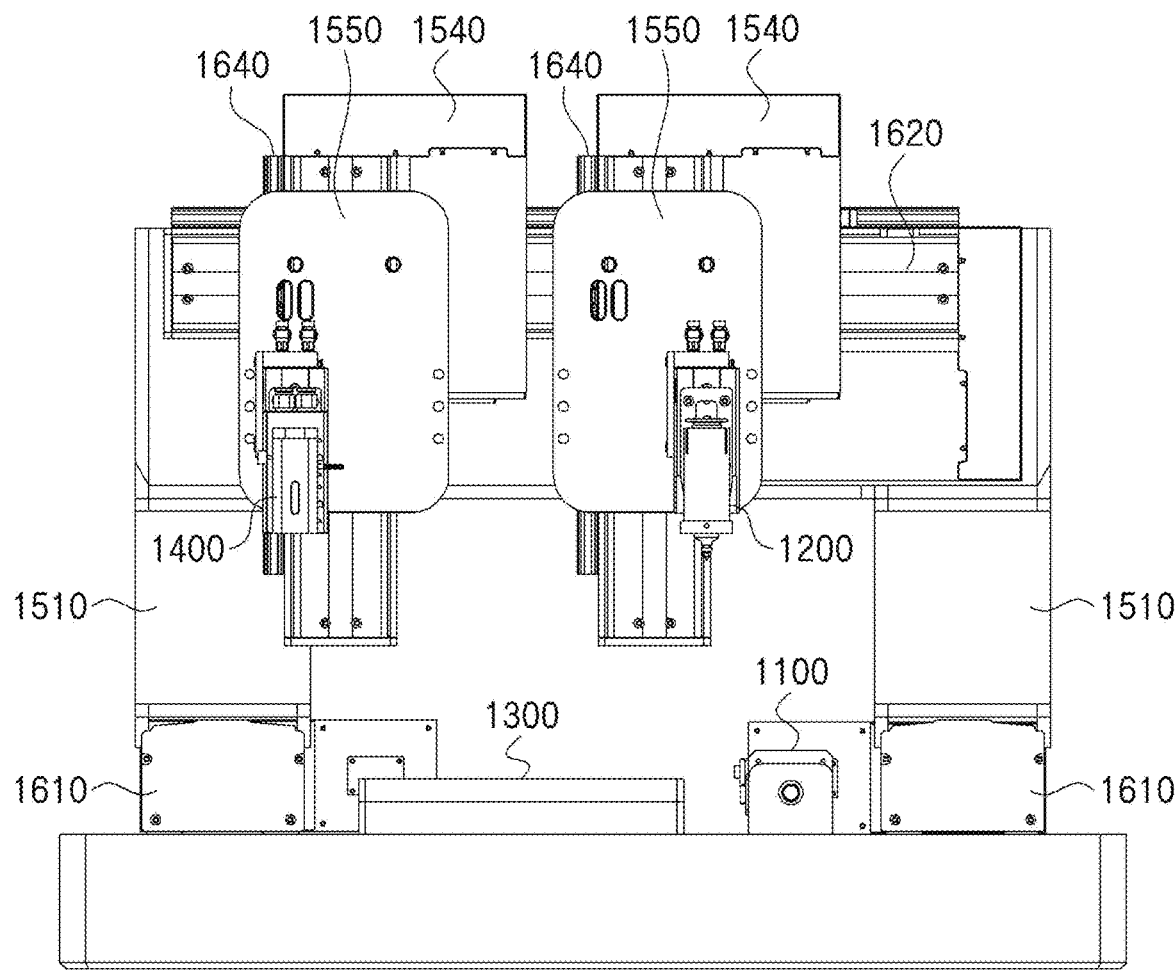

[FIG. 16a]
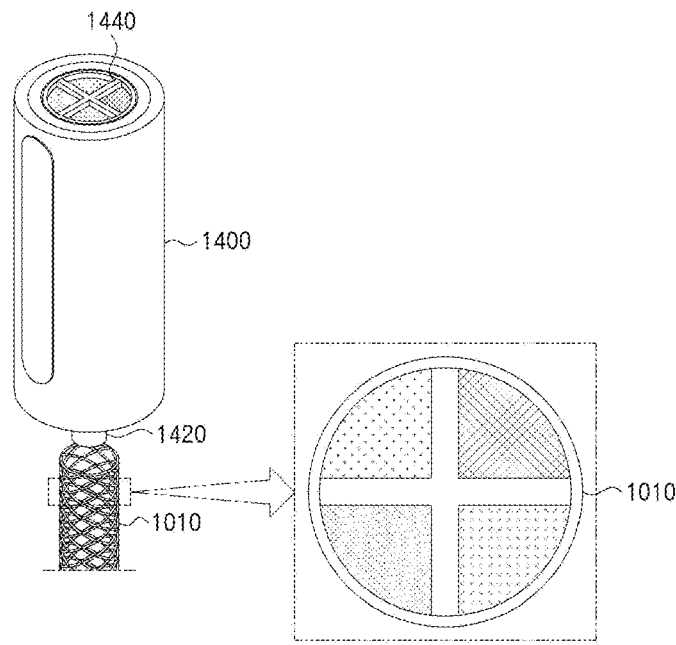
[FIG. 16b]
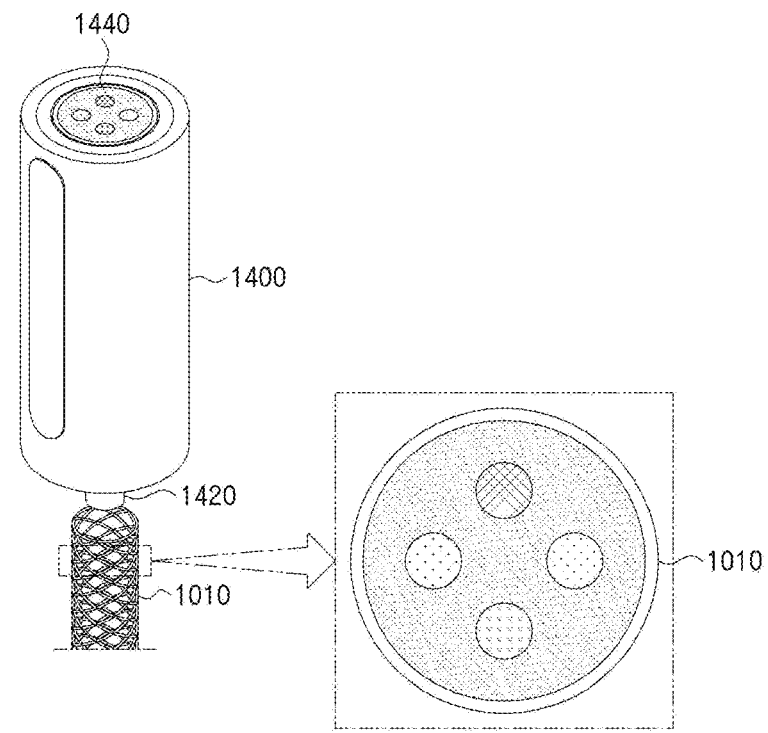

[FIG. 17a]
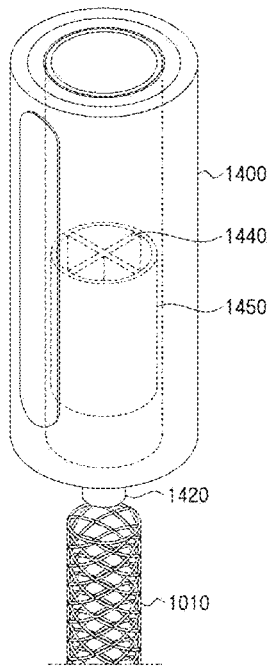
[FIG. 17b]
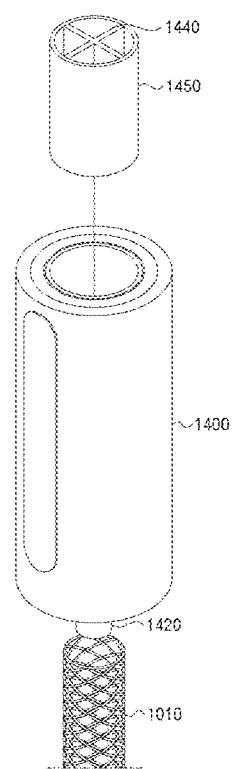

[FIG. 18]
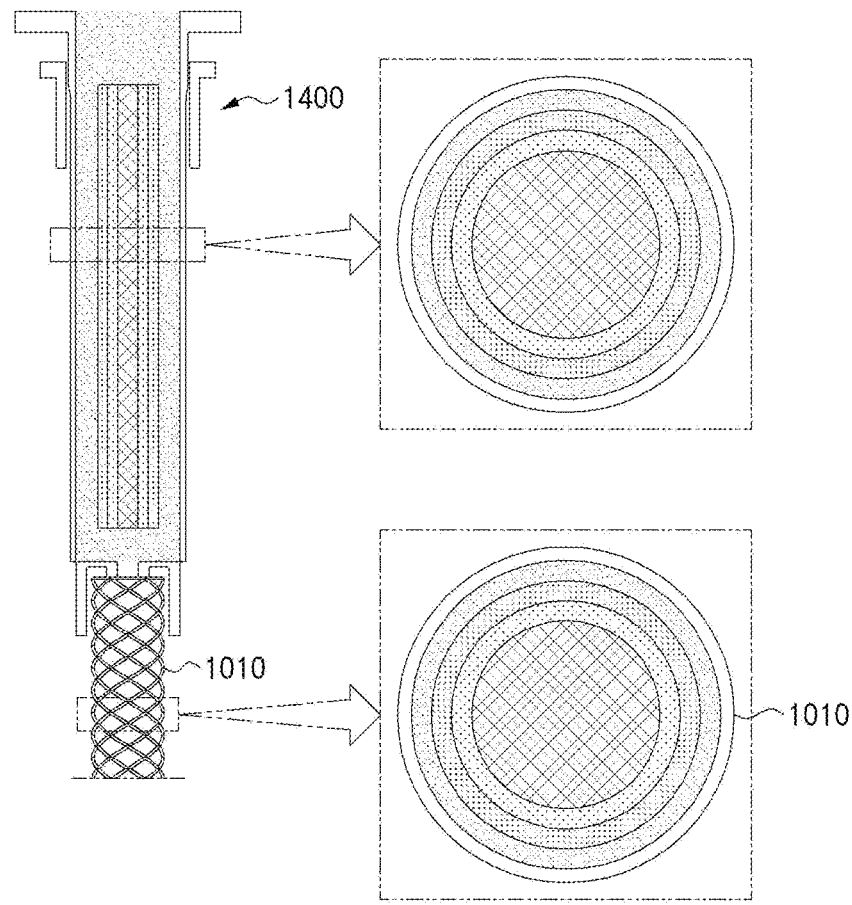
[FIG. 19]
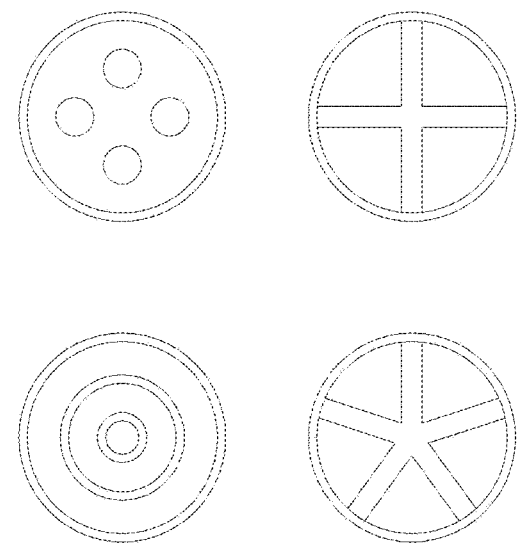

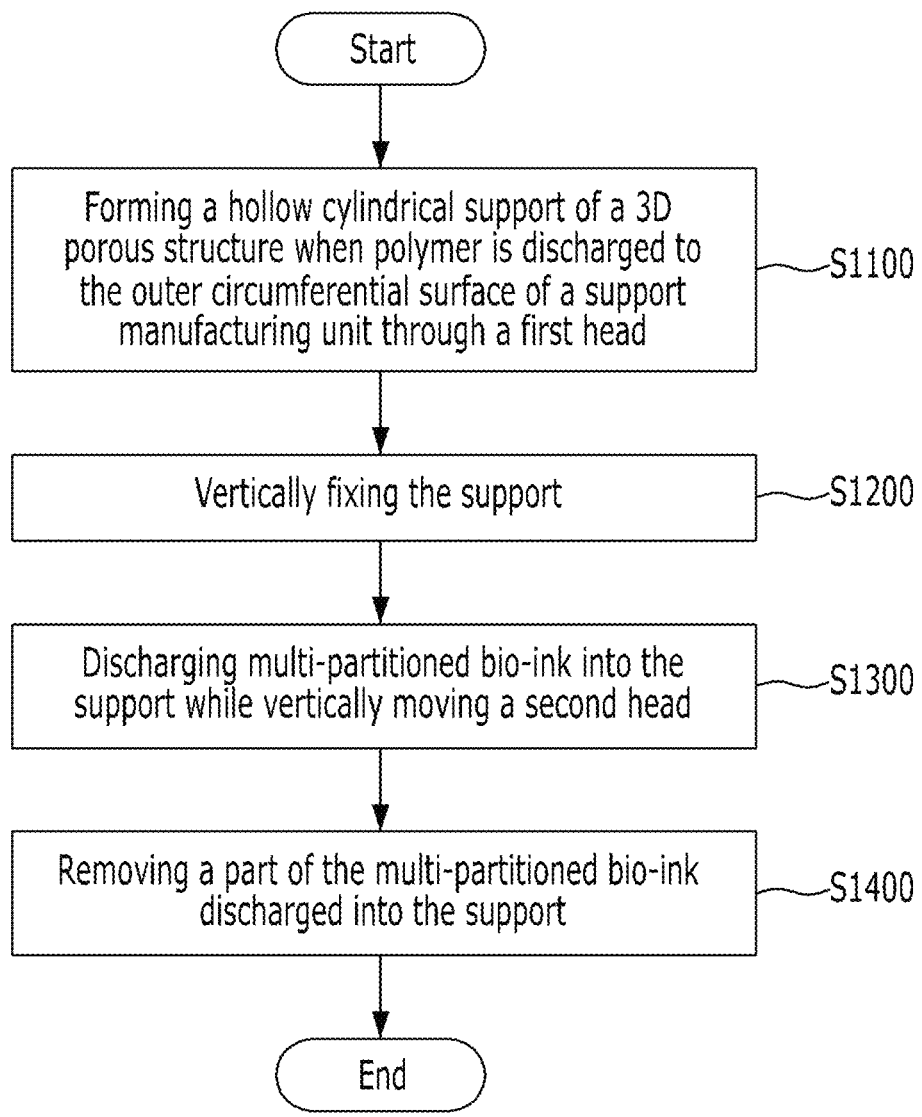
[FIG. 20]

[FIG. 21a]
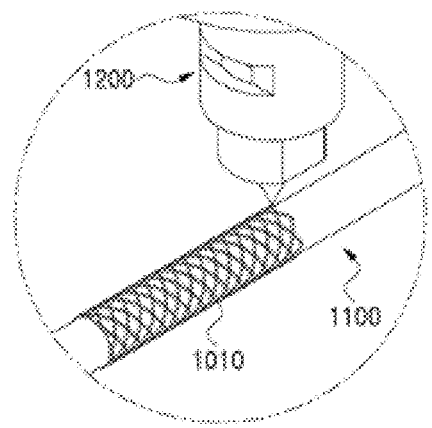
(a)
[FIG. 21b]
1010
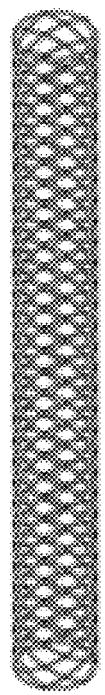
(b)

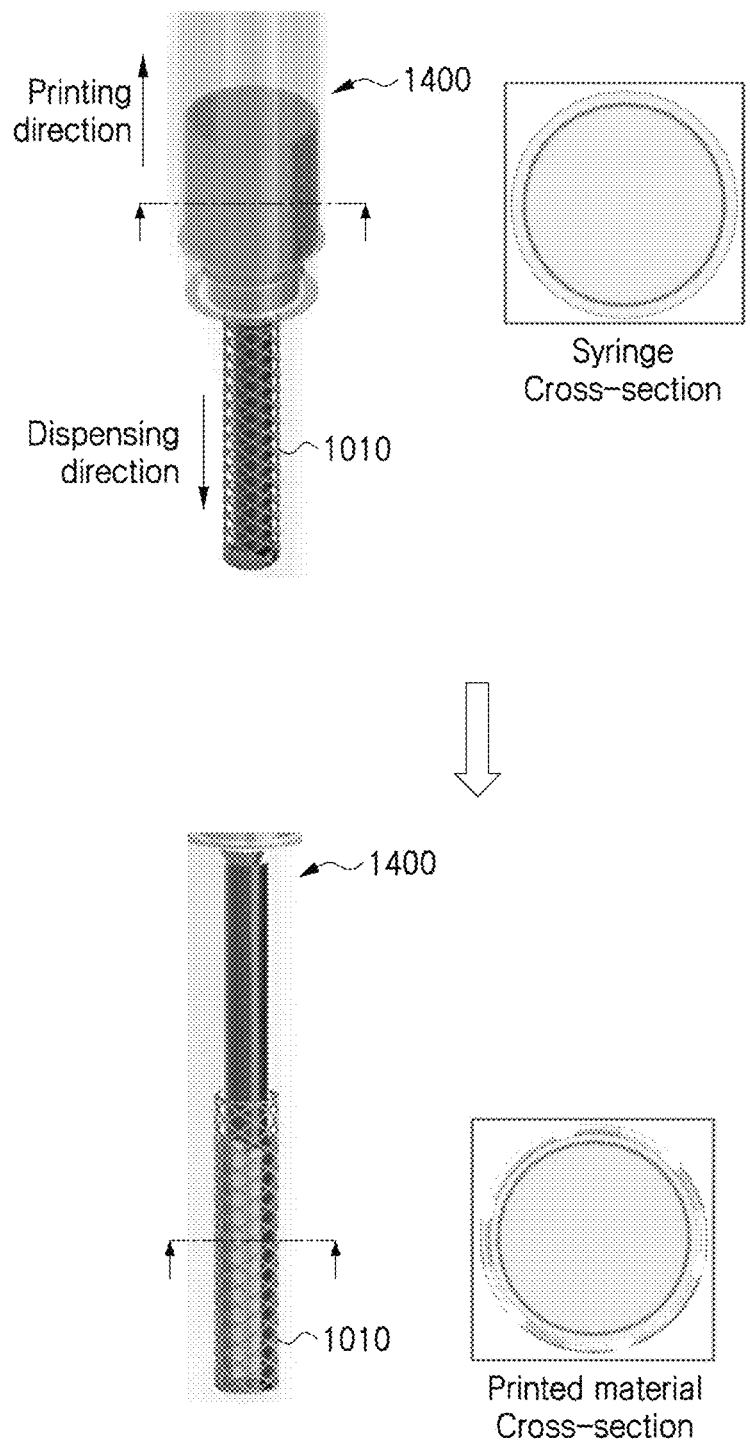
[FIG. 22]

[FIG. 23a]
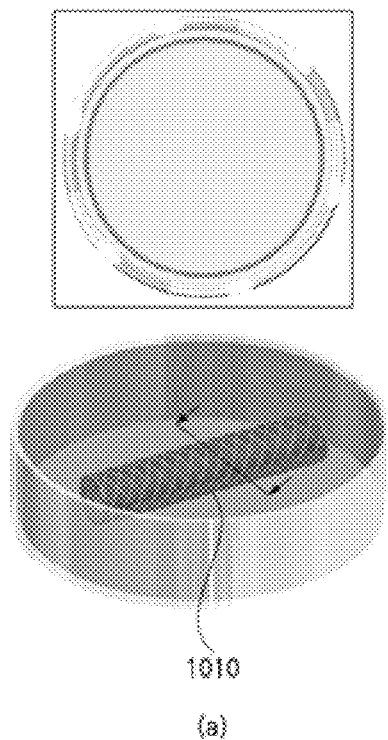
(a)
[FIG. 23b]
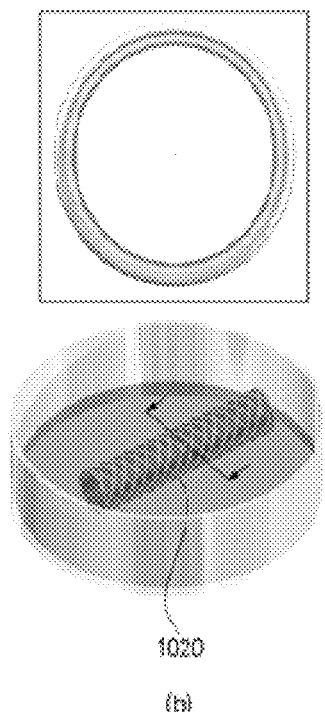
(b)

[FIG. 24]
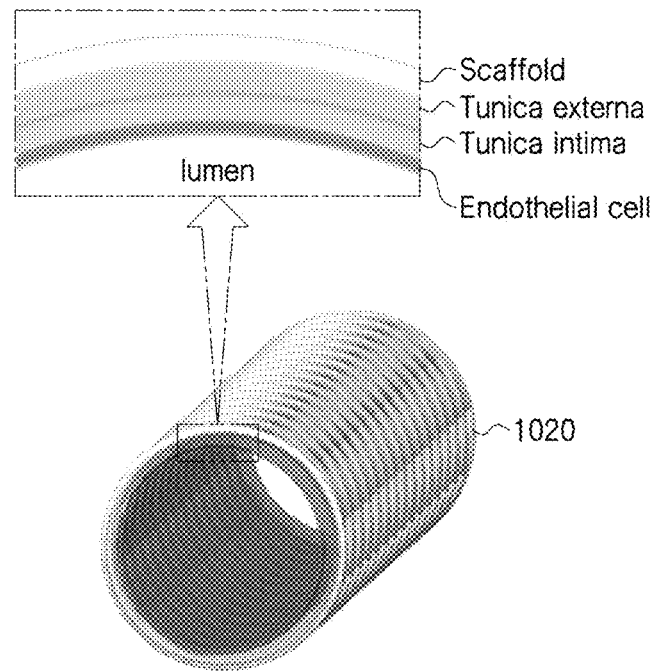
[FIG. 25]
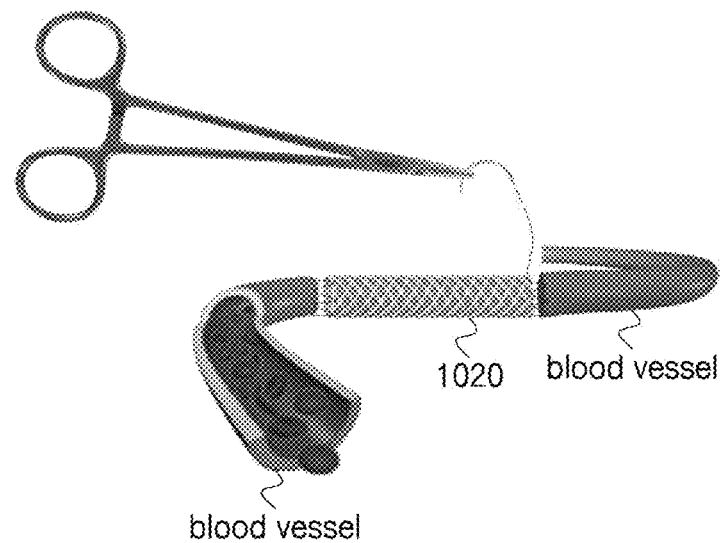

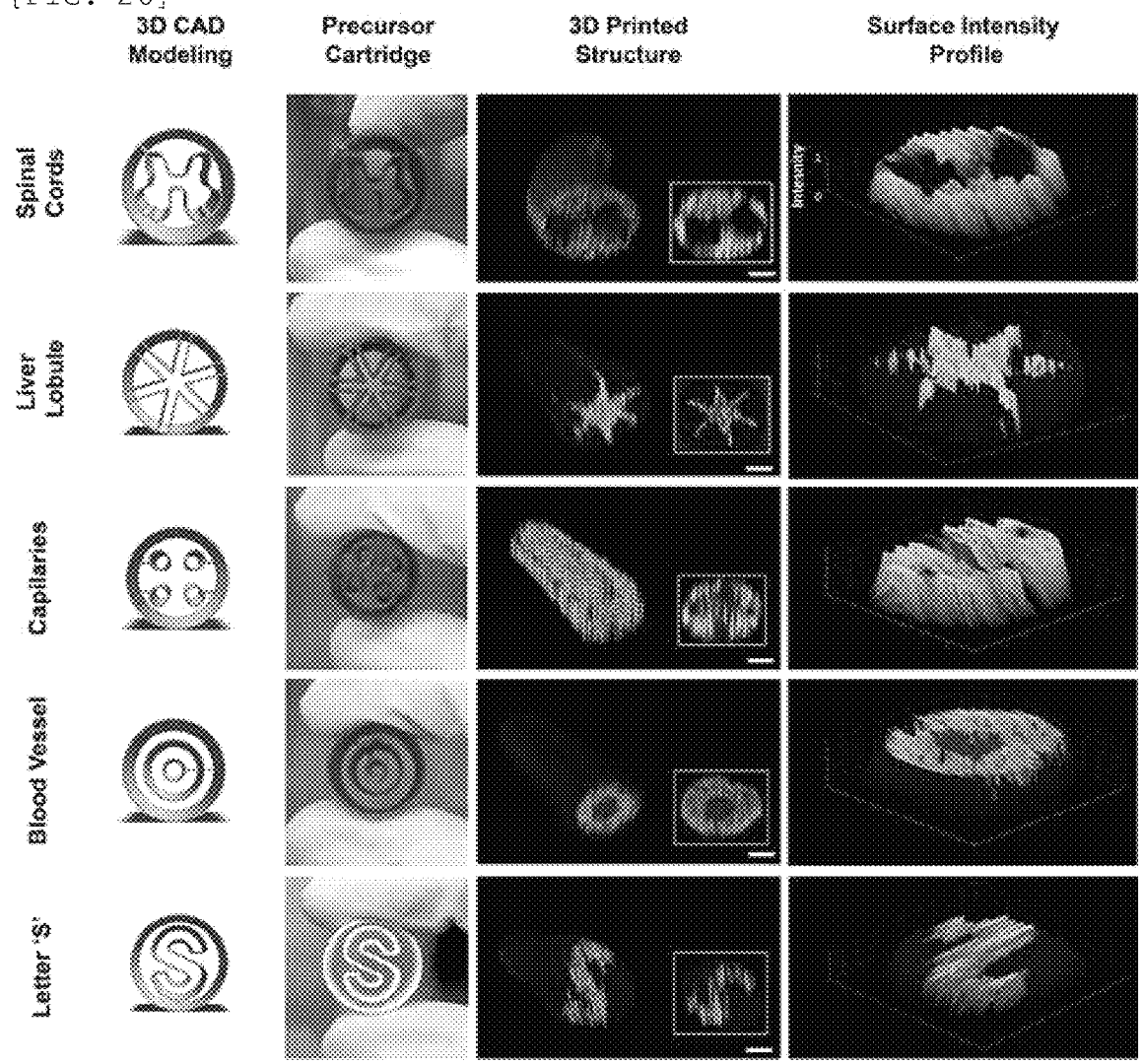

[FIG. 27]
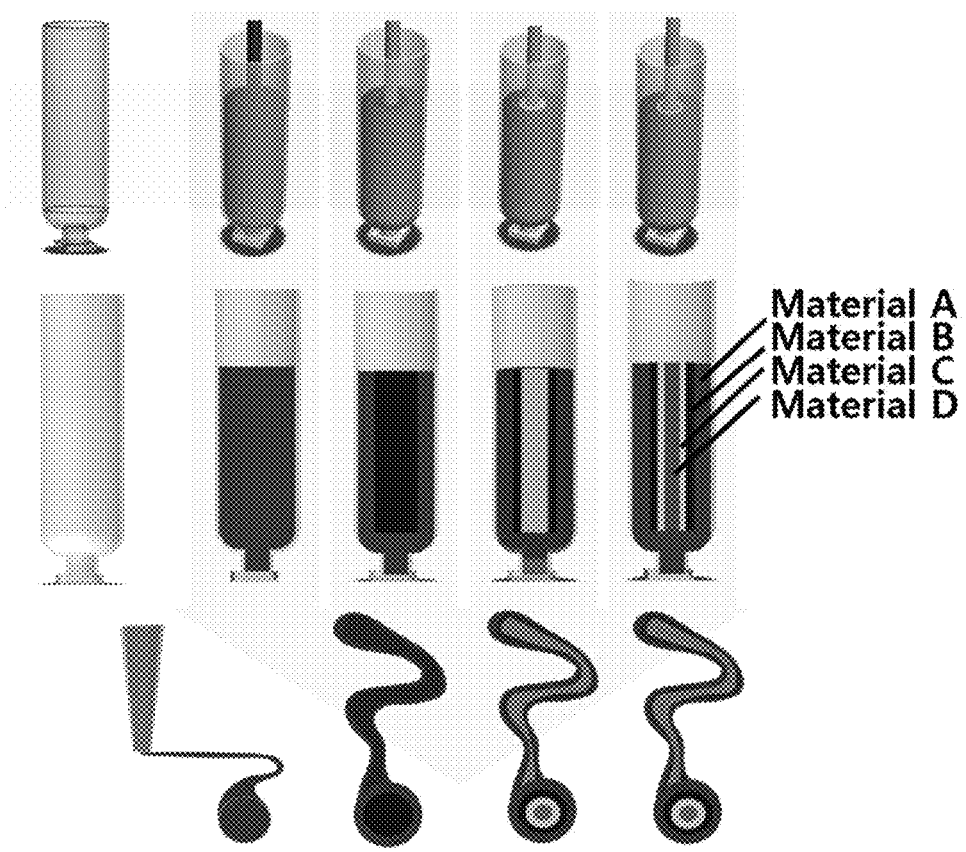

3D PRINTING SYSTEM FOR MANUFACTURING ARTIFICIAL BLOOD VESSEL AND METHOD FOR MANUFACTURING ARTIFICIAL BLOOD VESSEL USING SAME

CROSS-REFERENCE TO RELATED APPLICATIONS

This application is the U.S. National Phase under 35 U.S.C. § 371 of International Application No. PCT/KR2019/017877 filed on Dec. 17, 2019, which in turn claims the benefit of Korean Application No. 10-2019-0153497 filed on Nov. 26, 2019, the disclosures of which are incorporated by reference into the present application.

TECHNICAL FIELD

The present invention relates to a three-dimensional (3D) printing system for manufacturing an artificial blood vessel and a method for manufacturing an artificial blood vessel using the same, wherein a cylindrical support having a hollow 3D porous structure including a thermoplastic polymer is manufactured and vertically fixed, and hydrogel divided into at least two sections is discharged into the support, thereby maintaining the structure and shape constantly even after printing and manufacturing an artificial blood vessel having a multilayered hollow structure.

Moreover, the present invention relates to a support fixing device included in a molding plate on which a 3D printed matter is formed, and more particularly, to a molding plate including a support fixing device for supporting and fixing the support in order to perform 3D printing by discharging printing composite to the inside and the outside of the support and a 3D printer including the molding plate. The present invention is to provide a 3D printer wherein a hollow support is stably fixed in a printing area of the 3D printer inside and/or outside so as to stably perform 3D printing inside and/or outside the hollow support without rotation or movement of the support fixing device.

The work was supported by the Industrial Technology Innovation Program (No. 20000325) funded by the Ministry of Trade, Industry & Energy (MI, Korea)).

BACKGROUND ART

Cardiovascular disease that occurs in the circulatory system, such as the heart, the heart valve, and blood vessels has been ranked at the top in the cause of death of adults throughout the world, and out of them, blood vessel related diseases, such as arteriosclerosis, angina, cardiac infarction, cerebral stroke, etc., make up the largest number of the cause of death. Therefore, in order to maintain a patient's life and improve the quality of life, people demand a device to substitute for an autogenous vessel, such as a homograft vessel or an artificial vessel. Especially, studies for developing a device for manufacturing an artificial vessel using 3D bio-printing technology haven been under active progression. However, such a conventional tissue structure has a problem in that its cross section does not become round but is deformed when bio-printing is carried out on a flat plate since it does not have a support to be supported.

Especially, because blood vessel related diseases, such as arteriosclerosis, angina, cardiac infarction, cerebral stroke, etc., make up the largest number of the cause of death, in order to maintain a patient's life and improve the quality of life, people demand a device to substitute for an autogenous vessel, such as a homograft vessel or an artificial vessel. Especially, studies for developing a device for manufacturing an artificial vessel using 3D bio-printing technology haven been under active progression.

In order to manufacture an artificial vessel using 3D printing technology, a cylindrical support having a hollow 3D porous structure is manufactured and fixed, and then, printing composite is discharged to the inside and outside of the support.

However, such technology to precisely perform printing on a curved surface of the cylindrical or hollow structure still requires improvement. Especially, because the cylindrical support is fit to a cylindrical fixing support part to be fixed, in order to discharge printing composite into the support, a process of removing the fixing support part is necessarily accompanied. So, it is difficult to perform precise 3D printing. Furthermore, the conventional fixing support part has a limitation in fixing and supporting supports of various sizes since it is impossible to change the shape.

DISCLOSURE

Technical Problem

Accordingly, the present invention has been made in an effort to solve the above-mentioned problems occurring in the prior arts, and it is an object of the present invention to provide a three-dimensional (3D) printing system for manufacturing an artificial blood vessel and a method for manufacturing an artificial blood vessel using the same, wherein a cylindrical support having a hollow 3D porous structure including a thermoplastic polymer is manufactured and vertically fixed, and hydrogel divided into at least two sections is discharged into the support, thereby maintaining the structure and shape constantly even after printing and manufacturing an artificial blood vessel having a multilayered hollow structure.

It is an object of the present invention to provide a three-dimensional (3D) printer which includes a support fixing device and a rotary type 3D printing molding plate having the support fixing device, thereby performing a 3D printing process inside and/or outside the support easily and precisely by fixing a support using an internal fixing part located lower than the support to, and performing a 3D printing process more precisely and rapidly by stably and firmly fixing the support selectively using an external fixing part.

Technical Solution

To achieve the above objects, in an aspect of the present invention, the present invention provides a 3D printing system for manufacturing an artificial blood vessel comprising: a support manufacturing unit which is rotatable and forms a hollow cylindrical support of a 3D porous structure when polymer is discharged to the outer circumferential surface through a first head; a first head forming the hollow cylindrical support of the 3D porous structure by discharging polymer to a support manufacturing unit; a holder for vertically holding the cylindrical support manufactured through the first head; and a second head for discharging hydrogel, which is divided into at least two sections, into the cylindrical support vertically held and fixed on the holder.

Moreover, the first head comprises: a first pneumatic cylinder ascending and descending to discharge the polymer; a first discharge unit for discharging the polymer by lowering of the first pneumatic cylinder; and a temperature control unit for controlling temperature of the discharged polymer.

Furthermore, the second head comprises: a second pneumatic cylinder ascending and descending to discharge the polymer; a second discharge unit for discharging the hydrogel divided into at least two sections by lowering of the second pneumatic cylinder; and a temperature control unit for controlling temperature of the discharged hydrogel divided into at least two sections.

Additionally, the support manufacturing unit comprises: a rotary shaft which is rotatable when the polymer is discharged; a motor connected to one side of the rotary shaft to rotate the rotary shaft; and a bearing connected to the other side of the rotary shaft to support the rotary shaft.

In addition, the second head discharges the hydrogel divided into at least two sections into the cylindrical support vertically fixed on the holder.

Moreover, the holder is movable in a vertical direction while the fixed second head discharges the hydrogel divided into at least two sections.

Furthermore, the polymer is thermoplastic polymer, and the thermoplastic polymer is at least one selected from groups including lactide, caprolactone, glycolide, dioxanone, propylene, ethylene, vinylchloride, butadiene, methyl methacrylate, acrylic acid, 2-hydroxyethylmethacrylate, carbonate, and polyethylene terephalate.

Additionally, the hydrogel divided into at least two sections contains at least one selected from groups including polymer gels, cells, growth factors, and extracellular matrix, and a cross section of the hydrogel divided into the at least two sections discharged into the support 1010 and a cross section of the hydrogel divided into the at least two sections charged in the second pneumatic cylinder 1410 have the same pattern.

In the meantime, in another aspect of the present invention, the present invention provides a method for manufacturing an artificial blood vessel comprising the steps of: forming a hollow cylindrical support of a 3D porous structure by discharging polymer to the outer circumferential surface of a support manufacturing unit through a first head; vertically fixing the cylindrical support; and discharging hydrogel, which is divided into at least two sections, into the support while vertically moving a second head.

Moreover, the step of forming the support comprises the steps of: moving the first head above the support manufacturing unit; rotating the support manufacturing unit after locating the first head above the support manufacturing unit; and discharging the polymer to the outer circumferential surface of the support manufacturing unit while moving the first head in a longitudinal direction of the support manufacturing unit. In this instance, the rotating step and the discharging step are performed at the same time or performed in consecutive order.

In the meantime, the method for manufacturing an artificial blood vessel further comprises the step of removing a part of the hydrogel divided into at least two sections discharged into the support after the discharging step.

In another aspect of the present invention, the present invention provides a support fixing device for 3D printing comprising: a support plate on which a hollow cylindrical support is located; and an internal fixing part formed in the middle of the support plate, wherein the internal fixing part gets in contact with the inner circumferential surface of the support vertically located on the support plate in order to fix the support on the support plate.

The internal fixing part comprises: a tap hole disposed in the middle of the support plate; a bolt coupled with the tap hole; and an elastic tube disposed on the outer circumferential surface of the bolt, and the diameter of the bolt is smaller than the inner diameter of the support.

The elastic tube is an elastic body which is expandable in a radial direction when pressure is vertically applied by the bolt, and the elastic tube is made of at least one selected from groups containing silicone rubber, ethylene propylene rubber (EPM), ethylene propylene diene rubber (EPDM), chloroprene rubber (CR), thermoplastic elastomer (TPE), and thermoplastic olefin (TPO).

The support fixing device for 3D printing according to another embodiment of the present invention comprises an external fixing part formed on the upper surface of the support plate, wherein the external fixing part gets in contact with the outer circumferential surface of the support to fix the support.

The external fixing part comprises: a first fixing plate formed at one end of the upper surface of the support plate; a second fixing plate formed at the other end of the upper surface of the support plate; a guide for connecting the first fixing plate and the second fixing plate with each other; and a contact part which is movable along the guide.

In this instance, the contact part includes a contact groove formed in the surface coming into contact with the outer circumferential surface of the support.

Advantageous Effects

The three-dimensional (3D) printing system for manufacturing an artificial blood vessel and the method for manufacturing an artificial blood vessel using the same according to the present invention has an effect that the cylindrical support having the hollow 3D porous structure is manufactured and vertically fixed, and hydrogel divided into at least two sections is discharged into the support, thereby maintaining the structure and shape constantly even after printing and manufacturing an artificial blood vessel having a multilayered hollow structure. In addition, because the hollow cylindrical support has the 3D porous structure including the thermoplastic polymer, it has elasticity with a higher level, is not easily broken, and can be fixed to biological tissues with a thread by the porous structure of the support even in the case of clinical surgery.

The support fixing device according to the present invention can perform 3D printing inside and/or outside the support easily by fixing a support using the internal fixing part located at a low position, and can precisely perform 3D printing by firmly fixing the support using the external fixing part. Moreover, the support fixing device according to the present invention can three-dimensionally print supports of various sizes onto the hollow support precisely and rapidly by firmly and stably fixing the hollow support to an output stage of the 3D printer using the internal fixing part having the elastic tube and the external fixing part having the slidable contact part.

DESCRIPTION OF DRAWINGS

FIG. 1 is a view showing a 3D printer including a rotary type 3D printing molding plate having a support fixing device (A) according to an embodiment of the present invention.

FIG. 2 is an enlarged view of the molding plate having the support fixing device (A) to which a support is fixed according to the embodiment of the present invention.

FIG. 3 is a perspective view of the molding plate having the support fixing device (A) according to the embodiment of the present invention.

FIG. 4 is a sectional view of the support fixing device (A) having the support according to the present invention.

FIG. 5a and FIG. 5b are a mimetic diagram showing a principal that an internal fixing part according to the embodiment of the present invention fixes and operates the support according to the embodiment of the present invention.

FIG. 6a and FIG. 6b are a mimetic diagram showing the principal that an internal fixing part according to the embodiment of the present invention fixes and operates the support according to the embodiment of the present invention.

FIG. 7 and FIG. 8 are schematic diagrams showing modifications of the external fixing part.

FIG. 9 is a perspective view showing a 3D printing system for manufacturing an artificial blood vessel according to the present invention.

FIG. 10 is an enlarged view of a support manufacturing unit according to the present invention.

FIG. 11 is an enlarged view of a support according to the present invention.

FIG. 12 is an enlarged view of a first head and a second head according to an embodiment of the present invention.

FIG. 13 is an enlarged view of a support according to another embodiment of the present invention.

FIG. 14 is a front view showing a 3D printing system for manufacturing an artificial blood vessel according to another embodiment of the present invention.

FIG. 15 is a front view showing a 3D printing system for manufacturing an artificial blood vessel according to a further embodiment of the present invention.

FIG. 16a and FIG. 16b are a schematic diagram showing hydrogel charged in a second head (a) partitioned into four spaces or a second head (b) partitioned into five spaces.

FIG. 17a and FIG. 16b are an assembled view and FIG. 17(b) is an exploded view roughly showing a second head having a hollow part and a partitioning member according to another embodiment of the present invention.

FIG. 18 is a schematic diagram showing hydrogel divided into at least two sections according to another embodiment of the present invention.

FIG. 19 is an enlarged view showing the partitioning member used to the second head according to the embodiment of the present invention.

FIG. 20 is a flow chart showing a method for manufacturing an artificial blood vessel according to the present invention.

FIG. 21a and FIG. 21b are a schematic diagram showing a step of forming a hollow cylindrical support having a three-dimensional porous structure according to the present invention.

FIG. 22 is a schematic diagram showing a step of discharging the hydrogel, which is divided into the at least two sections, into the support.

FIG. 23a and FIG. 23b are a schematic diagram showing a step of removing some of the hydrogel, which is divided into the at least two sections and is discharged into the support.

FIG. 24 is a perspective view showing an artificial blood vessel according to the present invention.

FIG. 25 is a schematic diagram showing a process of clinically applying the artificial blood vessel according to the present invention.

FIG. 26 is a view showing a result that the hydrogel printed by the second head having the partitioning member with various shapes is observed through a confocal microscope.

FIG. 27 is a schematic view showing a blood vessel of a quadruple cylindrical structure is copied using hydrogel A, hydrogel B, hydrogel C, and hydrogel D without any partitioning member.

EXPLANATION OF REFERENCE NUMERALS

1: printing composite 3: head
4: head moving unit 5: stage
200: support plate 201: internal fixing part
202: external fixing part 203: bolt
204: screw part 205: elastic tube
206: tap hole 210: support fixing device
220: support 221: first fixing plate
222: second fixing plate 223: guide
225: contact part 225: contact groove
1001, 1002, 1003: 3D printing system for manufacturing artificial blood vessel
1010: support 1020: artificial blood vessel
1100: support manufacturing unit 1110: rotary shaft
1120: motor 1130: bearing
1200: first head 1210: first pneumatic cylinder
1220: first discharge unit
1230: temperature control unit
1300: holder 1310: fixing unit
1311: bolt 1312: elastic tube
1320: aperture 1321: hole
1330: elevating means 1400: second head
1410: second pneumatic cylinder
1420: second discharge unit
1430: temperature control unit 1440: partitioning member
1450: hollow part 1630, 1640: Z-axis stage
1510, 1520, 1530, 1540, 1550: head moving unit
1610: X-axis stage 1620: Y-axis stage

MODE FOR INVENTION

Hereinafter, reference will be now made in detail to the preferred embodiments of the present invention with reference to the attached drawings. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention.

In the entire specification of the present disclosure, when any portion "includes" any component, this does not exclude other components but means that any other component can be further included, unless stated otherwise. Moreover, the term of "part" in the specification means a unit or a block which carries out a specific function.

Steps may be carried out in a different order than described in the specification, unless a specific order is not stated contextually evidently. That is, the steps may be carried out in the same order described in the specification, may be carried out actually at the same time, or may be carried out in the opposite order.

An embodiment of the present invention relates to a fixing device which can vertically fix a hollow support on a station where three-dimensional (3D) printing is performed by a 3D printer. Unnecessary description on other components of the 3D printer will be omitted.

Hereinafter, a 3D printing molding plate having a hollow support fixing device will be described in more detail.

FIG. 1 is a view showing a 3D printer including a 3D printing molding plate having a support fixing device according to an embodiment of the present invention, and FIG. 2 is an enlarged view of the support fixing device of a hollow support fixing part (A) illustrated in FIG. 1.

As shown in FIGS. 1 and 2, the support fixing device 210 disposed on the 3D printing molding plate according to the present invention is disposed on a 3D printer and fixes and supports a hollow support 220 onto a printing stage. In this instance, preferably, the hollow support is a hollow cylindrical support, and especially, may be used more usefully in a 3D printing process of a printed structure which will be printed three-dimensionally onto an inner surface and an outer surface of the hollow cylindrical support, like an artificial blood vessel.

In more detail, the support 220 is fixed by the support fixing device 210 of the present invention, a printing composite 1 is discharged to the inside and/or outside of the support 220 in order, without movement of the fixed support, through a nozzle part 150 of a head of the 3D printer, so that a 3D structure having a structure or a form similar to an artificial blood vessel can be printed.

The head 3 having the nozzle part 150 of the 3D printer can move horizontally and vertically by a head moving unit 4, and the head moving unit 4 is guided by a stage 5.

The printing composite 1 is a liquid-state bio-ink material containing thermoplastic polymer, hydrogel, or mixture of thermoplastic polymer and hydrogel, and if necessary, cells may be added to the bio-ink material containing thermoplastic polymer or hydrogel.

In this instance, the thermoplastic polymer is not specially limited, but, for instance, may contain at least one selected from groups including lactide, caprolactone, glycolide, dioxanone, propylene, ethylene, vinylchloride, butadiene, methyl methacrylate, acrylic acid, 2-hydroxyethylmethacrylate, carbonate, and polyethylene terephalate.

Moreover, the bio-ink material such as hydrogel may be any one selected from groups including alginate, fibrinogen, carboxymethyl cellulose, heparin sulfate, hyaluronic acid, collagen, and dextran.

FIG. 3 is a perspective view of the molding plate having the support fixing device 210 according to the embodiment of the present invention, and FIG. 4 is a sectional view of the support fixing device 210.

Referring to FIGS. 3 and 4, the support fixing device 210 according to the present invention includes: a support plate 200, an internal fixing part 201 formed at the center of the support plate 200; and an external fixing part 202 formed on the upper surface of the support plate.

The support plate 200 is to support the support 220, and may be a disk shape as shown in FIG. 3, but is not limited to the above, and may be formed into one of various flat plates to support the support 220.

The support 220 may be a hollow cylindrical support, and preferably, a hollow cylindrical support with a porous structure. Such a support 220 may be manufactured in a 3D printing manner in advance using polymer, but may be formed in advance using a 3D printer having the support fixing device according to the present invention.

In this instance, the polymer material may be selected from groups including thermoplastic polymer capable of performing FDM printing, such as lactide, caprolactone, glycolide, dioxanone, propylene, ethylene, vinylchloride, butadiene, methyl methacrylate, acrylic acid, 2-hydroxyethylmethacrylate, carbonate, and polyethylene terephalate, acrylonitrile butadiene styrene (ABS), polycaprolactone (PCL), acrylonitrile-styrene-acrylate (ASA), stryrene-acrylonitrile copolymer (SAN), polystyrene (PS), polyphenylsulfone (PPSF/PPSU), polyetherimide, polylactic acid (PLA), poly-d-lysine (PDL), and others.

The internal fixing part 201 comes into contact with the inner circumferential surface of the support 220 to fix the support 220. The internal fixing part 201 includes: a tap hole 206 disposed in the middle of the support plate 200; a bolt 203 coupled with the tap hole 206; and an elastic tube 205 disposed on the outer circumferential surface of a screw part 204 of the bolt 203 (See FIG. 4).

As shown in FIG. 5, the elastic tube 205 gets in contact with the outer circumferential surface of the screw part 204 of the bolt 203 (FIG. 5(a)), and the bolt 203 pressurizes the elastic tube 205 from the top when being coupled with the tap hole 206 disposed in the middle of the support plate 200, so that the elastic tube 205 expands in a radial direction (See FIG. 5(b)). The elastic tube 205 expanding in the radial direction comes into contact with the inner circumferential surface of the support 220 so as to stably fix the support 220 in a vertical direction.

Concretely, the support 220 is located vertically so that the bolt 203 and the elastic tube 205 are included in an inner space thereof. After that, when the bolt 203 is coupled with the tap hole 206, the elastic tube 205 is pressurized downwards to expand in the radial direction and to come into contact with the inner circumferential surface of the support 220, so that the support 220 can be fixed onto the support plate 200 vertically. In this instance, preferably, a diameter of the bolt 203 is smaller than the inner diameter of the support 220, and the outer diameter of the elastic tube 205 expanded in the radial direction is equal to or similar to the inner diameter of the support 220.

A material of the elastic tube 205 is not limited specially, but preferably, is made of a material with elasticity so as to be changed in shape when being pressurized by the bolt 203. For instance, the elastic tube 205 may be made of at least one selected from groups containing silicone rubber, ethylene propylene rubber (EPM), ethylene propylene diene rubber (EPDM), chloroprene rubber (CR), thermoplastic elastomer (TPE), and thermoplastic olefin (TPO).

More preferably, a strain rate of the elastic material is within 25% to 35% in contrast to the initial diameter.

As described above, because the elastic tube 205 with elasticity gets in soft contact with the inner circumferential surface of the support 220, the support 220 is vertically fixed on the support plate 200 and it is prevented that the shape of the support 220 is damaged by pressure.

The external fixing part 202 according to the present invention gets in contact with the outer circumferential surface of the support 220 to fix the support 220. The external fixing part 202 includes: a first fixing plate 221 formed at one end of the upper surface of the support plate 200; a second fixing plate 222 formed at the other end of the upper surface of the support plate 200; a guide 223 connecting the first fixing plate 221 and the second fixing plate 222 with each other; and a contact part 224 formed to be movable along the guide 223.

As shown in FIG. 6, because the contact part 224 can move along the guide 223, after the support 220 is located vertically (FIG. 6(a)) so that the bolt 203 and the elastic tube 205 are included in the inner space of the support 220, when the contact part 224 is moved to get in contact with the outer circumferential surface of the support 220, the support 220 can be fixed more firmly in the vertical direction. The contact part 224 getting in contact with the outer circumferential surface of the support 220 is fixed by fixing means, such as a screw, a rubber ring, or adhesive resin so as to fix the support 220 more firmly.

The contact part 224 includes a contact groove 225 formed in the surface getting in contact with the outer circumferential surface of the support 220. The contact groove 225 is to fix the support 220 more firmly by widening a contact area between the contact part 224 and the support 220, and has the shape corresponding to the shape of the outer circumferential surface of the support 220. For instance, in case that the support 220 is a cylindrical support, the contact groove 225 may be formed in a curved shape having the radius of curvature which is the same as the support.

FIGS. 7 and 8 show various modifications of the external fixing part 202. FIG. 7 illustrates the contact part 224 of a damper shape which gets in contact with the outer circumferential surface of the support 220 to fix the support 220, and FIG. 8 illustrates the contact part 224 of a plate spring shape. It is preferable that the contact part 224 of the damper shape or the plate spring shape gets in contact with the outer circumferential surface of the support 220 to have three or more contact points formed on the outer circumferential surface of the support to support at least three areas of the support 220.

In order to prevent a lower end of a 3D structure finally formed by 3D printing from being damaged, a lower end of the support 220 getting in contact with the contact part 224 may be formed into a sacrificial layer.

As described above, the lower end of the support 220 fixed vertically is damaged by pressure applied due to contact of the contact part 224 or is damaged since load of the support 220 is inclined toward the lower end. So, the lower end of the support 220 is formed into the sacrificial layer, and then, the sacrificial layer is removed after completion of 3D printing so as to form a 3D structure without any damage. Preferably, the height of the sacrificial layer is within 10% relative to the entire height of the support 220, and more preferably, is less than 10 mm.

FIG. 9 is a perspective view showing a 3D printing system for manufacturing an artificial blood vessel according to the present invention. Referring to FIG. 9, the 3D printing system 1001 for manufacturing an artificial blood vessel according to the present invention includes: a support manufacturing unit 1100 which is rotatable and forms a hollow cylindrical support 1010 of a 3D porous structure when polymer is discharged to the outer circumferential surface through a first head 1200; the first head 1200 forming the hollow cylindrical support 1010 of the 3D porous structure when polymer is discharged to the support manufacturing unit 1100; a holder 1300 for vertically holding the cylindrical support 1010 manufactured through the first head 1200; a second head 1400 for discharging hydrogel, which is divided into at least two sections, into the cylindrical support 1010 vertically held and fixed on the holder 1300; head moving units 1510, 1520 and 1530 for moving the first head 1200 and the second head 1400 at the same time or individually in horizontal and vertical directions; and a X-axis stage 1610, a Y-axis stage 1620 and a Z-axis stage 1630 for guiding movement of the head moving unit 1500.

The support manufacturing unit 1100 is rotatable, and is rotated when polymer is discharged to the outer circumferential surface through the first head 1200, so that the support 1010 is formed in a hollow cylindrical shape of a 3D porous structure. Here, preferably, the diameter of the outer circumferential surface is equal to or similar to the diameter of a human blood vessel.

The first head 1200 is moved along the Y-axis stage 1620 by the head moving unit 1520 and is located above the support manufacturing unit 1100. After that, the first head discharges polymer to the outer circumferential surface of the support manufacturing unit 1100 while moving along the X-axis stage 1610. During the discharge process of the polymer, the support manufacturing unit 1100 is rotated at the same time. That is, because the polymer is discharged and the support manufacturing unit 1100 is rotated at the same time, the support 1010 can be formed in the hollow cylindrical shape of the 3D porous structure.

Moreover, it is preferable that the first head 1200 can discharge the polymer by pneumatic pressure, and pneumatic pressure is controlled properly according to concentration of the polymer or the size of a nozzle of the first head 1200 so as to control a discharge rate or discharge speed of the discharged polymer.

In the meantime, preferably, the polymer is thermoplastic polymer, and is biodegradable polymer which is harmless inside or outside a living body and easily adjusts to intravital environment without any adverse reaction.

The thermoplastic polymer is not specially limited, but may contain at least one selected from groups including lactide, caprolactone, glycolide, dioxanone, propylene, ethylene, vinylchloride, butadiene, methyl methacrylate, acrylic acid, 2-hydroxyethylmethacrylate, carbonate, and polyethylene terephalate.

The support 1010 including thermoplastic polymer can constantly maintain the structure and the form even after printing, has elasticity of a predetermined level, and is not easily damaged. Furthermore, the support 1010 can be fixed to biological tissues with a thread by the porous structure even in the case of clinical surgery (Refer to FIG. 25).

The holder 1300 vertically fixes the support formed in the support manufacturing unit 1100 by the first head 1200, so that the second head 1400 can discharge hydrogel divided into at least two sections into the support 1010.

Preferably, the holder 1300 includes a temperature control system therein to maintain proper temperature while the support 1010 is fixed vertically. For instance, the holder 1300 can control temperature using a Peltier module. In this instance, the temperature control system can check temperature at every predetermined interval by an automatic corrector and correct temperature to be proper.

The second head 1400 discharges hydrogel divided into at least two sections into the support 1010 fixed on the holder 1300 while moving in the vertical direction, and the hydrogel divided into at least two sections is layered into the support 1010, so that an artificial blood vessel 1020 can be manufactured.

As an example, the second head 1400 moves along the Y-axis stage 1620 by the head moving unit 1520, and is located above the support 1010 which is held vertically and fixed on the holder 1300. After that, the second head 1400 discharges hydrogel divided into at least two sections into the support 1010 while ascending along the Z-axis stage 1630. So, the cross section of the hydrogel divided into at least two sections and discharged into the support 1010 and the cross section of the hydrogel divided into at least two sections and charged in the second head 1400 have the same pattern. However, sizes of the cross sections may vary according to the diameter of the support 1010.

The term "the same" is defined as meaning not only that it is 100% equal but also that it is identical enough to actually perform the same function. That is, 'the cross section has the same pattern' means that just the size of the cross section varies but the original form of the cross section is maintained as it is.

Additionally, the second head 1400 can discharge hydrogel divided into at least two sections by pneumatic pressure without any partitioning part, and pneumatic pressure is properly controlled according to concentration of the hydrogel divided into the at least two sections (without any partitioning part) or the size of the nozzle of the second head 1400, so that the discharge rate or discharge speed of the hydrogel divided into the at least two sections can be adjusted.

Meanwhile, the hydrogel divided into at least two sections means hydrogel where two or more different inks are not mixed together but are partitioned into several sections. The different inks mean that at least one selected from groups containing ingredients, and contents and properties of the ingredients is different. Detailed description about the hydrogel divided into the at least two sections will be described later.

The head moving units 1510, 1520 and 1530 move along the X-axis stage 1610, the Y-axis stage 1620 or the Z-axis stage 1630 to move the first head 1200 and the second head 1400 at the same time in the horizontal and vertical directions, and the X-axis stage 1610, the Y-axis stage 1620 and the Z-axis stage 1630 guide movement of the head moving units 1510, 1520 and 1530.

In detail, preferably, the first head 1200 and the second head 1400 are formed on the head moving unit 1530, and moves in the vertical direction along the Z-axis stage 1630 simultaneously while the hydrogel divided into the at least two sections is discharged from the second head 1400.

FIG. 10 is an enlarged view of the support manufacturing unit 1100 according to the present invention. The support manufacturing unit 1100 includes a rotary shaft 1110, a motor 1120, and a bearing 1130.

The rotary shaft 1110 rotates when thermoplastic polymer is discharged from the first head 1200, so that the support 1010 is formed in a hollow cylindrical shape of a 3D porous structure. Here, Preferably, the rotary shaft 1110 is manufactured in such a way that the diameter of the rotary shaft 1110 is equal to or similar to the diameter of the human blood vessel.

The motor 1120 is connected to one side of the rotary shaft 1110 and serves to rotate the rotary shaft 1110 by receiving driving power from the outside, and the bearing 1130 is connected to the other side of the rotary shaft 1120 to support the rotating rotary shaft 1120.

In detail, the rotary shaft 1110 may be separated from the motor 1120 and the bearing 1130, so that the hollow cylindrical support 1010 having the 3D porous structure made of thermoplastic polymer formed on the outer circumferential surface of the rotary shaft 1110 by being discharged from the first head can be separated from the rotary shaft 1110.

FIG. 11 is an enlarged view of the first head and the second head according to the present invention. As shown in FIG. 11, the first head 1200 includes a first pneumatic cylinder 1210, a first discharge unit 1220, and a temperature control unit 1230.

The first pneumatic cylinder 1210 ascends or descends by pneumatic pressure transferred from the outside so that the thermoplastic polymer is discharged through the first discharge unit 1220. That is, the first pneumatic cylinder 1210 applies pressure to the thermoplastic polymer while lowering by pneumatic pressure properly controlled according to concentration of the thermoplastic polymer or according to the size of a nozzle of the first discharge unit 1220, then, the thermoplastic polymer is discharged to the outer circumferential surface of the support manufacturing unit 1100 through the first discharge unit 1220.

Preferably, the first pneumatic cylinder 1210 properly controls pneumatic pressure according to concentration of the thermoplastic polymer or the size of the nozzle of the first discharge unit 1220 so as to control the discharge rate or discharge speed of the thermoplastic polymer discharged.

The first discharge unit 1220 is pressurized by descent of first pneumatic cylinder 1210 so as to discharge the thermoplastic polymer to the outer circumferential surface of the support manufacturing unit 1100. In this instance, the first discharge unit 1220 discharges the thermoplastic polymer to the outer circumferential surface of the rotating support manufacturing unit 1100 while moving along the X-axis stage 1610, then, a hollow cylindrical support 1010 of the 3D porous structure can be manufactured.

The temperature control unit 1230 serves to control temperature so that the thermoplastic polymer has proper viscosity, and can control temperature properly depending on thermoplastic polymer used.

In the meantime, the second head 1400 includes a second pneumatic cylinder 1410, a second discharge unit 1420, and a temperature control unit 1430. The second pneumatic cylinder 1410 ascends or descends by pneumatic pressure transferred from the outside so that hydrogel is discharged through the second discharge unit 1420. As occasion demands, single hydrogel which is not divided or hydrogel which is divided into at least two sections may be discharged.

In this instance, pressure is applied to the hydrogel divided into the at least two sections while the hydrogel divided into the at least two sections lowers by pneumatic pressure controlled properly according to concentration of the hydrogel or the size of a nozzle of the second discharge unit 1420, so that the hydrogel divided into the at least two sections can be discharged into the support through the second discharge unit 1420.

The second pneumatic cylinder 1410 controls pneumatic pressure properly according to concentration of the hydrogel divided into the at least two sections or according to the size of the nozzle of the second discharge unit 1420, so that the discharge rate or discharge speed of the hydrogel divided into the at least two sections can be controlled.

The second discharge unit 1420 is pressurized by descent of the second pneumatic cylinder 1410 so as to discharge the hydrogel divided into the at least two sections into the support.

In this instance, the second discharge unit 1420 can discharge the hydrogel divided into the at least two sections into the support 1010 while ascending along the Z-axis stage 1630. In addition, when the support 1010 moves while the holder 1300 on which the support 1010 is fixed vertically moves, it is also possible to discharge the hydrogel divided into the at least two sections into the support 1010 through the second discharge unit 1420.

As a result, a cross section of the hydrogel divided into the at least two sections discharged into the support 1010 and a cross section of the hydrogel divided into the at least two sections charged in the second pneumatic cylinder 1410 can have the same pattern.

The temperature control unit 1430 serves to control temperature so that the hydrogel divided into the at least two sections has physical properties and biological properties for 3D processing, and it is preferable to control temperature properly depending on hydrogel used.

FIG. 12 is an enlarged view of a support according to an embodiment of the present invention, and FIG. 13 is an enlarged view of a support according to another embodiment of the present invention.

First, referring to FIG. 12, the support 1300 includes a fixing unit 1310 for vertically fixing the support 1010, and the fixing unit 1310 includes a bolt 1311 and an elastic tube 1312.

The bolt 1311 pressurizes the elastic tube 1312 to expand the elastic tube 1312 when the elastic tube 1312 gets in contact with the outer circumferential surface of a screw part 1311-a and is coupled with a nut (not shown) located at a lower portion. The expanded elastic tube 1312 comes into contact with the inner circumferential surface of the support 1010 to fix the support 1010 vertically.

Concretely, the support 1010 is located vertically so that the bolt 1311 and the elastic tube 1312 is included in an inner space. After that, when the bolt 1311 is coupled with the nut, the elastic tube 1312 is pressurized and expanded and is supported closely to the inner circumferential surface of the support 1010, so that the support 1010 can be fixed vertically. In this instance, it is preferable that the diameter of the bolt 1311 is smaller than that of the support 1010 and the outer diameter of the expanded elastic tube 1312 is equal to or similar to the inner diameter of the support 1010.

The elastic tube 1312 gets in contact with the outer circumferential surface of the bolt 1311, namely, the screw part 1311-a, and gets in contact with the inner circumferential surface of the support 1010 by being expanded in a radial direction by being pressurized when the bolt 1311 is coupled with the nut located at the lower portion.

A material of the elastic tube 1312 is not specially limited, but preferably, is made of a material with elasticity to be changed in shape when being pressurized by the bolt 1311. For instance, the elastic tube may be made of silicone rubber, alginate, gelatin, and so on.

That is, when the elastic tube 1312 with elasticity gets in soft contact with the inner circumferential surface of the support 1010, the support 1010 is firmly fixed in the vertical direction, and at the same time, it is prevented that the shape of the support 1010 is damaged by external pressure.

Meanwhile, for another example, as shown in FIG. 13, the holder 1300 includes an aperture 1320 for vertically fixing the support 1010. After the support 1010 is vertically located in a hole 1321 formed in the aperture 1320, when the aperture 1320 is controlled to get in contact with the outer circumferential surface of the support 1010, the support 1010 can be fixed vertically. In this instance, in order to prevent the lower end of the support 1010 from being damaged when getting in contact with the aperture 1320, the lower end of the support 1010 getting in contact with the aperture 1320 may be formed as a sacrificial layer.

FIG. 14 is a front view showing a 3D printing system for manufacturing an artificial blood vessel according to another embodiment of the present invention.

Referring to FIG. 14, the 3D printing system 1002 for manufacturing an artificial blood vessel includes a support manufacturing unit 1100, a first head 1200, a holder 1300, an elevating means 1330, a second head 1400, head moving units 1510, 1520 and 1530, an X-axis stage 1610, a Y-axis stage 1620, and a Z-axis stage 1630. Here, description of the same parts as the afore-mentioned embodiment will be omitted, and just different parts will be described.

The holder 1300 vertically fixes the support 1010 formed by the first head 1200 and the support manufacturing unit 1100, and is moved in a vertical direction while the second head 1400 discharges the hydrogel divided into the at least two sections into the support 1010, so that single hydrogel or the hydrogel divided into the at least two sections is layered inside the support 1010.

Concretely, the holder 1300 includes the elevating means 1330, for instance, a pneumatic cylinder, a hydraulic cylinder, a screw or the likes, disposed at a lower portion to lift up or lower down the holder 1300. While the second head 1400 discharges the hydrogel divided into the at least two sections into the support 1010, the hydrogel divided into the at least two sections is layered inside the support 1010 while performing movement, such as ascent and descent, by the elevating means 1330. In this instance, the cross section of the hydrogel divided into at least two sections and discharged into the support 1010 and the cross section of the hydrogel divided into at least two sections and charged in the second head 1400 have the same pattern.

The second head 1400 discharges the hydrogel divided into at least two sections into the support 1010 fixed on the holder 1300 moved in the vertical direction, and the hydrogel divided into at least two sections is layered inside the support 1010, so that an artificial blood vessel 120 can be manufactured.

Concretely, the second head 1400 is moved along the Y-axis stage 1620 by the head moving unit 1520 to be located above the support 1010. After that, the second head 1400 discharges the hydrogel divided into at least two sections into the support 1010, so that the cross section of the hydrogel divided into at least two sections and discharged into the support 1010 and the cross section of the hydrogel divided into at least two sections and charged in the second head 1400 have the same pattern.

FIG. 15 is a front view showing a 3D printing system for manufacturing an artificial blood vessel according to a further embodiment of the present invention. Referring to FIG. 15, the 3D printing system 1003 for manufacturing an artificial blood vessel includes a support manufacturing unit 1100, a first head 1200, a holder 1300, a second head 1400, head moving units 1510, 1540 and 1550, an X-axis stage 1610, a Y-axis stage 1620, and a Z-axis stage 1640. Here, description of the same parts as the afore-mentioned embodiment will be omitted, and just different parts will be described.

The head moving units 1510, 1540 and 1550 move along the X-axis stage 1610, the Y-axis stage 1620 or the Z-axis stage 1640 to individually move the first head 1200 and the second head 1400 in horizontal and vertical directions, and the X-axis stage 1610, the Y-axis stage 1620 and the Z-axis stage 1640 guide movements of the head moving units 1510, 1540 and 1550. Concretely, it is preferable that the second head 1400 is formed on the head moving unit 1550, so that the second head 1400 can move in the vertical direction along the Z-axis stage 1640 while discharging the hydrogel divided into the at least two sections.

In the meantime, FIGS. 16 to 19 schematically illustrate the hydrogel divided into the at least two sections according to various embodiments of the present invention. Referring to FIGS. 16 to 19, the hydrogel divided into the at least two sections may be formed by different inks charged in partitioned spaces of the second head 1400 which has two or more partitioned spaces.

Concretely, the inside of the second head 1400 has a plurality of spaces partitioned to receive ink therein. In this instance, the second head 1400 may be manufactured in a single form to have the specific number of spaces or may be partitioned into a plurality of spaces by a partitioning member 1440 detachable from the second head 1400. In case that the partitioning member 1440 detachable from the second head 1400 is used, when just the partitioning member 1440 is changed from the single second head 1400, the hydrogel divided into the at least two sections can be printed with patterns of various kinds, and the size of the spaces partitioned by the partitioning member 1440 can be controlled according to an area ratio of each ink.

In case that the partitioning member 1440 removable to be detachable from the second head 1400 is used, the partitioning member 1440 can be inserted into the second head 1400 as shown in FIGS. 16(*a*) and 16(*b*), or can be inserted into the second head 1440 by being mounted together with a hollow part 1450 as shown in FIGS. 17(*a*) and 17(*b*).

In this instance, the partitioning member 1440 may be manufactured in various ways, such as injection, pressing, 3D printing or others, but preferably, may be manufactured in the 3D printing manner. The partitioning member 1440 is good enough in size and shape, for instance, a cylindrical shape, a rectangular shape, a triangular pyramid shape, or the likes, if the partitioning member 1440 can enter the second head 1400. That is, a cross section pattern of the partitioning member 1440 may be manufactured in various shapes, and preferably, may have the same pattern as the cross-sectional area of the artificial blood vessel to be manufactured. FIG. 19 illustrates examples of various cross-sectional forms of the partitioning member 1440, and the partitioning member 1440 may be similar in shape to an artificial blood vessel or may have shapes having a plurality of concentric circles. Moreover, the partitioning member is made of thermoplastic resin capable of FDM printing of acrylonitrile butadiene styrene (ABS), polycaprolactone (PCL), acrylonitrile-styrene-acrylate (ASA), styrene-acrylonitrile copolymer (SAN), polystyrene (PS), polyphenylsulfone (PPSF/PPSU), polyetherimide, polylactic acid (PLA), poly-d-lysine (PDL), and so on, photocurable resin, and solid materials, such as nonferrous/nonferrous alloy materials.

In another embodiment of the present invention, referring to FIG. 18, the hydrogel divided into the at least two sections may be provided to the second head 1400 as an ink printed matter by printing ink of at least one kind through 3D printing, and additionally provided to the second head 1400 as an ink filling material of ink of at least one kind by a method otherwise the 3D printing. Here, the ink printed matter printed by the 3D printing may have a 2D or 3D pattern by itself. Furthermore, differently from the ink printed matter provided to the second head 1400, the ink filling material means ink filling material provided not by 3D printing but by a filling method. The filling method otherwise 3D printing is, for instance, a method of filling using a tube, a syringe or others, and is not specially limited to the above.

Meanwhile, a difference in ink viscosity between the ink filling material and the ink printed matter provided to the second head 1400 is less than 5,000 cp when ink viscosity is measured at temperature of 25° C., for instance, 0 to 5,000 cp, less than 1,000 cp, less than 500 cp, less than 200 cp, less than 150 cp, less than 100 cp, or less than 50 cp.

If the ink viscosity difference is very big, the shape of the ink printed matter may be transformed by molecular force of different materials. In the case of performing 3D printing through discharge, if the same pressure is applied to the ink or the second head 1400, due to a viscosity difference, the pattern of the hydrogel divided into the at least two sections received in the second head 1400 may collapsed. Therefore, if two or more different kinds of ink are used, smaller differences in viscosity are preferable.

Moreover, a difference in elasticity value between the ink filling material and the ink printed matter may be less than 10,000 Pa, for instance, 0 Pa to 10,000 Pa. Preferably, the ink filling material and the ink printed matter are similar in development of changes according to shear velocity and the viscosity value and the elasticity value are similar to each other.

Furthermore, if polymer gels used for the different kinds of ink are different, for instance, the polymer gels are temperature-sensitive like collagen or gelatin but the other polymer gels are not temperature-sensitive like alginate or fibrin gel, it is necessary to control temperature of the inside of the second head 1400, and it is preferable to properly control temperature of the second head 1400 within a range of 4° C. to 37° C.

In the embodiment illustrated in FIGS. 16 and 18, in order to prevent the hydrogel divided into the at least two sections charged in the second head 1400 from being poured down, after about 0.1 mL to 2 mL of hydrogel is previously put in the second head 1400 as a supporting material, the hydrogel divided into the at least two sections is put in the second head 1400. After that, hydrogel is recharged in the second head 1400 in order to induce stable printing.

Additionally, the hydrogel divided into the at least two sections is pressurized through the second pneumatic cylinder 1410, and is discharged into the support 1010 through the second discharge unit 1420. In this instance, the second pneumatic cylinder 1410 is controlled such that the cross section of the hydrogel divided into the at least two sections is reduced in size while maintaining the same shape.

In detail, in order to apply pressure to the ink received in each partitioned space under the same conditions, pressure is applied using just one second pneumatic cylinder 1410 or the same pressure is applied using two or more second pneumatic cylinders 1420.

After that, different inks are discharged into the support 1010 through the nozzle having a single passage by pressurization of the second pneumatic cylinder 1410, and the cross section of the hydrogel divided into the at least two sections discharged into the support 1010 and the cross section of the hydrogel divided into the at least two sections charged in the second pneumatic cylinder 1410 can have the same pattern.

Here, if pressure applied to the second pneumatic cylinder 1410 is too high, load applied to the nozzle becomes larger and it occurs a damage, or the hydrogel divided into the at least two sections is not smoothly discharged in the form of a thread but is unevenly discharged in a lump. If applied pressure is too weak, because of resistance by viscosity of the hydrogel divided into the at least two sections, the hydrogel may not be smoothly discharged from the nozzle.

Additionally, the nozzle of the second discharge unit 1420 has a single passage, and so, can discharge the hydrogel divided into the at least two sections not by a multiple channel control but by a single channel control. If the diameter of the nozzle is too small, there still exist risks caused by strong pressure since discharge pressure is increased. If the diameter of the nozzle is too big, when an artificial blood vessel is manufactured, precision of a 3D shape may be deteriorated.

Therefore, it is preferable that the hydrogel divided into the at least two sections is discharged by the nozzle having an outlet diameter within a range of 0.1 mm to 1 mm under pressure of 0.1 kPa to 500 kPa. It is also preferable that the second head 1400 prints the hydrogel divided into the at least two sections while moving at speed within a range of 1 to 700 ram/min.

Within the above-mentioned pressure range and diameter range, the hydrogel divided into the at least two sections can be discharged smoothly and easily, and precision of a 3D shape of the artificial blood vessel manufactured can be achieved at a desired level.

Like the conventional arts, in the case that one material is injected to perform bio-printing, because there is a limitation in reduction of the size of the inner diameter of the nozzle of the second discharge unit 1420, there is a limitation in reduction of volume of materials. However, the present invention can perform more precise injection than the conventional art since volume of ink discharged can be reduced in proportion to the number of various inks.

In addition, because a contact area between ink and the inner surface of the passage of the second discharge unit 1420 becomes reduced when the hydrogel divided into the at least two sections passes the nozzle of the second discharge unit 1420, generated shearing stress is reduced in comparison with discharge of a single material. Therefore, the present invention is more advantageous than the conventional arts in an aspect of cell activity.

Therefore, the present invention can print and manufacture artificial blood vessels having a complex cross-sectional structure with high precision and resolution, manufacture artificial blood vessels having various cross-sectional patterns, print desired shapes differently, and raise a cell survival rate by greatly reducing shearing stress of cells.

Moreover, in case that the hydrogel divided into the at least two sections is used, compared with the conventional arts using multiple heads containing different multiple materials, the present invention can reduce printing time by using the single head and simplify the 3D printing system since performing printing by discharging two or more different inks using one head, namely, the second head 1400.

In the meantime, as shown in FIG. 18, the cross section of the hydrogel divided into the at least two sections discharged into the support 1010 and the cross section of the hydrogel divided into the at least two sections charged in the second pneumatic cylinder 1410 can have the same pattern, and a ratio of the cross-sectional pattern of the hydrogel divided into the at least two sections charged in the second head 1400 may be indicated by various methods, such as an area ratio of cross section, a diameter ratio, or others.

In detail, a ratio of the cross section pattern of the hydrogel divided into the at least two sections charged in the second head 1400 and the cross section pattern of the hydrogel divided into the at least two sections discharged into the support 1010 may be, for instance, 100:99 to 100:0.1, 100:50 to 100:1, or 100:18 to 100:1 to reduce the diameter of the cross section pattern.

However, the reduction ratio is directly influenced by the cross-section diameter of the second head 1400, the cross-section diameter of the second discharge unit 1420, or the diameter of the nozzle, and can be designed in various ways by being properly adjusted according to the size of the cross-section pattern of the support 1010.

According to the embodiment of the present invention, the ratio can be reduced to 98.7% from the entire diameter of a specific shape to be miniaturized. For instance, the reduction ratio may be calculated by the following equation 1.

Reduction ratio=100−(cross section diameter of second head/cross section diameter of printed matter)×100(%) [Equation 1]

In the meantime, it is preferable that the ink provided to the second head 1400 is bio-ink capable of manufacturing an artificial blood vessel. In the present invention, 'bio-ink' contains living cells or bio-molecules, and is a common name of materials capable of manufacturing artificial blood vessels using 3D printing technology for manufacturing artificial blood vessels. The bio-ink according to the present invention includes liquid, semisolid, or solid composition containing a plurality of cells.

Furthermore, the bio-ink must provide physical properties for 3D process and biological environment for performing the cells' target function. It is preferable to properly supply nutrition and oxygen necessary for living of the cells in the second head 1400 if the printing process gets longer. Additionally, the bio-ink can protect the cells from physical stress generated during the printing process. In addition, the bio-ink must have physical properties necessary for the printing process, such as repeatability and productability of 3D patterning, non-blocking of the nozzle, and others.

Therefore, the bio-ink is preferably hydrogel, and the hydrogel divided into the at least two sections may contain at least one selected from groups including polymer gels, cells, growth factors, and extracellular matrix. For instance, the hydrogel may be hydrogel in which desired cells are mixed, hydrogel containing specific growth factors, hydrogel containing cells and growth factors, hydrogel containing cytokine, or combination thereof.

Preferably, the hydrogel is polyethylene glycol, collagen, Matrigel, alginate, gelatin, agarose, fibrinogen, and tissue-derived cell ink, or mixture thereof. The cells are vascular endothelial cells, vascular smooth muscle cells or fibrous cells derived from a patient to which an artificial blood vessel is grafted or inserted, or are at least one selected from groups including vascular endothelial cells, vascular smooth muscle cells or fibrous cells differentiated from stem cells derived from the patient.

Moreover, the hydrogel divided into the at least two sections has viscosity thicker than water (1 cp) since rapidly spreading at low viscosity, and gel-state materials having viscosity of 2 cp to 1,000,000 cp, for instance, 2 cp to 10,000 cp or 5 cp to 1,000,000 cp, when being measured at temperature of 25° C. are suitable for the hydrogel. Furthermore, the hydrogel divided into the at least two sections may use various viscosity boosters in order to provide viscosity appropriate for discharge.

The hydrogel divided into the at least two sections is excellent at physical and biological aspects, such as bio-compatibility, printing suitability, geometrical precision, and accuracy.

In the meantime, densification of the hydrogel divided into the at least two sections is induced from growth of cells at proper density, and the hydrogel divided into the at least two sections additionally contains tissue-derived ingredients for densification.

The tissue-derived ingredients mean decellularization of specific tissues of an animal, such as blood vessels, cartilage, kidney, heart, liver, muscles and others and gelation of materials based on extracellular matrix, and are to strengthen tissue specificity of the hydrogel divided into the at least two sections.

Moreover, the hydrogel divided into the at least two sections may further include cell culture media. The cell culture media are a concept including media suitable for target cells.

There are various kinds of polymer gel solutions. The polymer solutions require the following conditions. First, the polymer gel solutions must have proper viscosity to perform 3D printing well so as to be easily discharged to the nozzle, and must be rapidly hardened after being discharged so as to prevent the shape of an object from being collapsed. Additionally, the polymer solutions must create cell culture environment similar to tissues in the human body.

The polymer gel may be at least one selected from groups including fucoidan, collagen, alginate, chitosan, hyaluronic acid, polycarprolactone, polyetherimide, nylon, polyaramid, polyvinyl alcohol, polyvinylpyrrolidone, poly-benzyl-glutamate, polyphenyleneterephthalamide, polyaniline, polyacrylonitrile, polyethylene oxide, polystyrene, cellulose, polyacrylate, polymethylmethacrylate, polylactic acid (PLA), polyglycolic acid (PGA), polylactide-polyglycolic acid copolymer (PLGA), poly(ethylene oxide terephthalate)-co-butylene terephthalate (PEOT/PBT), polyphosphoester (PPE), polyphosphagen (PPA), polyanhydride (PA), poly (orthoester (POE), poly (propylene fumarate)-diacrylate (PPF-DA), and poly (ethylene glycol) diacrylate (PEG-DA), or combination of the above-mentioned materials. However, the materials are not limited to the above.

The polymer gels may use chemically modified natural polymers, for instance, GelMA that gelatin and methacrylate are coupled chemically and photoinitiator is coupled, alginate/gelatin, and alginate in which pentapeptide sequencing Tyr-Ile-Gly-Ser-Arg (YIGSR) and EDC/NHS are combined to add binding site of alginate may be used.

Especially, the hydrogel, such as polyethylene glycol, alginate, collagen and gelatin, has been widely used in manufacturing a carrier in which cells are contained since being high in water content, is excellent at bio compatibility, being capable of controlling mechanical features, and is excellent at biodegradability. Therefore, the hydrogel is very suitable for manufacturing a cell-mounted structure, and can be directly printed to obtain a tissue recovery frames of various types.

The gelatin is especially suitable as a cell delivery material since being temperature-sensitive. That is, gelatin is liquefied at 37° C. and is solidified at temperature less than normal temperature.

The polymer gel may form a cross-link bond using physical treatment or chemical treatment, and can use a bridge solution for the chemical treatment and selectively use the bridge solution according to selected polymer gel.

For instance, the bridge solution may be plaster; or a mixture solution of at least one kind selected from hydroxyapatite (HA), carbonate apatite, fluorapatite, chloroapatite, α-TCP, β-TCP, calcium metaphosphate, calcium-4-phosphate, calcium hydrogen phosphate, calcium hydrogen-2-phosphate, calcium pyrophosphate, calcium carbonate, calcium sulfate, and 1-ethyl-3(3-3-dimethylaminopropyl) carbodiimide hydrochloride (EDC), or may be a solution of mixture of at least one selected from salts thereof.

Preferably, the ink containing the polymer gel solution is formed such that a collagen concentration ratio in a liquid-state collagen solution is within a range of 0.1 to 30% by weight.

A method for manufacturing hydrogel may be performed applying the manufacturing method used when ink is manufactured by general 3D printing, but is not limited specially.

The hydrogel divided into at least two sections may contain cells as described above, and the cells may be vascular endothelial cells, vascular smooth muscle cells or fibrous cells derived from a patient to which an artificial blood vessel is grafted or inserted, or are at least one selected from groups including vascular endothelial cells, vascular smooth muscle cells or fibrous cells differentiated from stem cells derived from the patient.

The cells used in the hydrogel divided into at least two sections may be cultivated in an optional manner known in the related field. Cell and tissue cultivation methods are known in the related field.

The cells may be cultivated together with cell differentiation materials inducing differentiation of cells according to desired cell lines. For instance, stem cells are incubated in contact with differentiation media to generate cell types of a predetermined range.

The stem cells may be incubated in contact with differentiation media, for instance, including an osteogenic differentiation media, chondrogenic differentiation media, adipogenic differentiation media, neuronal differentiation media, myocardial cell differentiation media, and vascular cell differentiation media.

Additionally, the cells can be cultivated together with growth factors, cytokine, and others. The growth factors are called protein containing cytokine, polypeptide, or polypeptide complex, which is generated by cells and has an influence on itself or various neighboring cells or cells away from it. In general, the growth factors have an influence on growth and/or differentiation of cells of a specific type spontaneously or by reacting to a number of biochemical or environmental stimuli. A part of the growth factors are hormones.

For instance, the growth factors are insulin, insulin-like growth factors (IGF), nerve growth factors (NGF), vascular endothelial growth factors (VEGF), keratinocyte growth factors (KGF), fibroblast growth factors (FGF) including basic FGF (bFGF), platelet-derived growth factors (PDGF) including PDGFAA and PDGF-AB, bone morphogenetic protein (BMP) including BMP-2 and BMP-7, hepatocyte growth factors (HGF), transforming growth factor-alpha (TGF-α), transforming growth factor-beta (TGF-β) including TFGβ-1 and TGFβ-3, epidermal growth factors (EGF), granulocyte-macrophage colony-stimulating factors (GM-CSF), granulocyte colony stimulating factors (G-CSF), interleukin-6 (IL-6), IL-8, and so on.

The number of cells contained in the hydrogel divided into at least two sections used to manufacture an artificial blood vessel can be adjusted according to kinds of cells, nutritional content of the cells contained in the bio-ink composite, and so on.

Moreover, kinds of the cells contained in the hydrogel composite divided into at least two sections can be varied in various ways according to kinds of blood vessels to be manufactured by the above-mentioned method. A person having ordinary skill in the art to which the present invention pertains may select and apply proper cells according to kinds of blood vessels to be manufactured by 3D bio-printing.

Furthermore, after the hydrogel divided into at least two sections is discharged and layered into the support, when it is heated or is exposed to UV rays or a cross link solution is added, it may promote cross link of the hydrogel divided into at least two sections. Such cross link helps the hydrogel divided into at least two sections to be completed as a harder structure, and a photoinitiator may be used in order to promote the cross link.

In the meantime, in another embodiment of the present invention, the present invention relates to a method for manufacturing an artificial blood vessel (See FIG. 20). The method for manufacturing an artificial blood vessel includes: a step (S100) of discharging polymer to the outer circumferential surface of the support manufacturing unit through the first head and forming a hollow cylindrical support of a 3D porous structure; a step (S200) of vertically fixing the support; a step (S300) of discharging the hydrogel divided into at least two sections into the support while vertically moving the second head; and a step (S400) of removing a part of the hydrogel divided into at least two sections discharged into the support. An artificial blood vessel having a hollow multilayered structure can be manufactured through the method for manufacturing an artificial blood vessel according to the present invention.

As shown in FIG. 21, in the step (S100) of forming a hollow cylindrical support of a 3D porous structure, polymer is discharged to the outer circumferential surface of the support manufacturing unit 1100 through the first head 1200 (See FIG. 21(a)). Therefore, the hollow cylindrical support 1010 of the 3D porous structure (See FIG. 21(b)) is formed. The step (S100) includes a step (S110) of moving the first head above the support manufacturing unit. In this instance, the first head 1200 is moved along the Y-axis stage 1620 to be located above the support manufacturing unit 1100.

Next, the step (S100) includes a step (S120) of rotating the support manufacturing unit. After the rotating step (S120), the step (S100) further includes a step (S130) of discharging the polymer to the outer circumferential surface of the support manufacturing unit while moving the first head in a longitudinal direction of the support manufacturing unit. Preferably, the rotating step (S120) and the discharging step (S130) are preferably carried out simultaneously or in consecutive order. The support manufacturing unit 1100 rotates when the first head 1200 discharges polymer to the outer circumferential surface of the support manufacturing unit 1100 while moving along the X-axis stage 1610, so that a hollow cylindrical support of the 3D porous structure can be formed. After that, a step (S200) of vertically fixing the support formed through the above steps is carried out, and preferably, the support 1010 can be vertically fixed on the holder 1300.

Next, a step (S300) of discharging the hydrogel divided into at least two sections into the support while moving the second head vertically is carried out. Referring to FIG. 22, the step (S300) is carried out after moving the second head 1400 above the support 1010. That is, the second head 1400 moves along the Y-axis stage 1620 (See FIG. 21) by the head moving unit 1520 and is located above the support 1010. After that, the second head 1400 discharges the hydrogel divided into at least two sections into the support 1010 while ascending vertically. Therefore, the cross section of the hydrogel divided into at least two sections and discharged into the support 1010 and the cross section of the hydrogel divided into at least two sections and charged in the second head 1400 have the same pattern.

Finally, as shown in FIG. 23, a step (S400) of removing a part of the hydrogel divided into at least two sections discharged into the support is carried out. Here, because the hydrogel divided into at least two sections discharged into the support 1010 includes a material of one or more kinds and has a multilayer structure, it is preferable to remove a part of the hydrogel corresponding to a middle part by changing gelation conditions of materials forming each layer.

As an example, based on the cross section of the hydrogel divided into at least two sections, sodium alginate of 3 w/v % is formed outside, an artificial blood vessel formed with gelatin of 3%, which is hydrogel temperature-sensitive, is cross-linked to calcium chloride of 200 M inside. After that, when the hydrogel is put in a liquid of 37° C. (See FIG. 23(a)), alginate gel maintains its shape as it is, but gelatin is melted down so that a hollow artificial blood vessel 20 is formed (See FIG. 23(b)).

Referring to FIGS. 24 and 25, the artificial blood vessel 1020 manufactured according to the present invention is manufactured in the form of a hollow multilayered shape, and can uniformly maintain the structure and the form of the artificial blood vessel 1020 even after printing. Additionally, since the artificial blood vessel includes the hollow support of the 3D porous structure including thermoplastic polymer, it has excellent elasticity, is not easily damaged, and can be fixed to biological tissues with a thread by the porous structure of the support even in the case of clinical surgery.

Hereinafter, embodiments of the present invention will be described. However, the scope of the present invention is not limited to the preferred embodiments, and a person having ordinary skill in the art to which the present invention pertains may modify the embodiments in various ways from the contents described in this specification without departing from the scope of the present invention.

[Embodiment 1] Printing of Hydrogel Divided by Partitioning Part

In order to perform 3D printing using the second head divided by a partitioning part, a partitioning member was manufactured using polyactic acid (PLA) through 3D printing.

In this instance, a 3D printer using the second head was used, sizes of the nozzle were 18, 20, 22, 25 and 27 gauges, and a printed state of RGB hydrogel was check by a confocal microscope. It was confirmed that the 3D printer could be miniaturized in the same shape as the cross section of the second head.

According to the embodiment of the present invention, the ratio showed that the printed matter could be miniaturized from a specific shape (example: the entire diameter (15 mm) of Lobule) up to 98.7% (200 μm), the result was adjusted in Table 1, and the reduction ratio was calculated as in the Equation 1.

$$\text{Reduction ratio} = 100 - (\text{second head diameter/printed diameter}) \times 100(\%) \quad [\text{Equation 1}]$$

TABLE 1

| Div. | Second head | Nozzle | | | | |
|---|---|---|---|---|---|---|
| Inner diameter | 15 mm | 0.83 mm | 0.62 mm | 0.41 mm | 0.25 mm | 0.2 mm |
| Printing diameter | 15 mm | 1 mm | 0.725 mm | 0.55 mm | 0.375 mm | 0.2 mm |
| Reduction(%) | — | 93.4 | 95.2 | 96.4 | 97.5 | 98.7 |
| Reduction ratio | — | 100:15 | 100:11 | 100:3.7 | 100:2.5 | 100:1.3 |

[Embodiment 2] Printing of Hydrogel Divided into at Least Two Sections with Various Shapes In order to perform 3D printing using the second head having the partitioning part of various shapes, the partitioning member of various shapes was manufactured using polyactic acid (PLA) through 3D printing.

After sodium alginate of 3 w/v % containing green, blue and red fluorescent particles was put into the second head having the partitioning member, a printed state of RGB hydrogel was check by a confocal microscope.

FIG. 26 shows the result that the printed state of RGB hydrogel using the second head having the partitioning member of various shapes was observed by a confocal microscope.

As shown in FIG. 26, as the result of performing printing through the second head using the partitioning member of various shapes modeled through a 3D CAD, an output having the same partitioned structure could be printed, and tissues of various forms could be copied.

[Embodiment 3] Second Head Including Ink Printed Matter and Ink Filling Material First hydrogel for filling made of 3 w/v % of sodium alginate was injected into the second head of the 3D printer. Sodium alginate of 3 w/v % containing green fluorescent particles was injected into the second head, in which the first hydrogel was injected, as second hydrogel by 3D printing using the 3D printer having a long nozzle.

The first hydrogel for filling and the second hydrogel 3D-printed were printed by the 3D printing method using the output obtained through the second discharge unit by applying pressure. They were printed in three lines using the nozzle size (nozzle I.D) of 1.0 mm. In case that the nozzle having the nozzle size (nozzle I.D) of 1.0 mm was used, the cross section printed was 30 µm in length. In case that the nozzle having the nozzle size (nozzle I.D) of 2 mm was used, the cross section printed was 70 µm in length.

As a result that the output was observed by a confocal microscope, the printed state of the hydrogel containing green fluorescent particles was checked by the confocal microscope. As the result that the discharged output was fluorescently observed by the confocal microscope, ink was printed at high resolution.

[Embodiment 4] Printing of Hydrogel Divided into at Least Two Sections Using Nozzle of Various Sizes The 3D printer using the second head like the third embodiment was used, sizes of the nozzle were 18, 20, 22, 25 and gauges, and a printed state of hydrogel was check by a confocal microscope. In detail, the inner diameter of each nozzle of 18, 20, 22, 25 and 27 gauges was 0.82 mm, 0.63 mm, 0.41 mm, 0.28 mm and 0.1 mm.

As a result that printed outputs of the first hydrogel filling material and the second hydrogel printed matter according to a change in size of the nozzle using the second discharge unit were observed by the confocal microscope, it was confirmed that the 3D printer could be miniaturized in the same shape as the cross section of the second head. According to the embodiment of the present invention, the ratio showed that the printed matter could be miniaturized from a specific shape (example: the entire diameter (15 mm) of Lobule) up to 98.7% (200 µm), the result was adjusted in Table 2, and the reduction ratio was calculated as in the Equation 2.

$$\text{Reduction ratio of ink printed matter} = (A-B)/A \times 100 \; (\%) \quad \text{[Equation 2]}$$

(in Equation 2, A is a cross section diameter of the first ink printed matter provided to the second head by 3D printing, B is a cross section diameter of the second ink printed matter, and A and B have the same length unit.)

TABLE 2

| | | | | | |
|---|---|---|---|---|---|
| Cross section diameter(mm) of second head | 9.3 mm | 9.3 mm | 9.3 mm | 9.3 mm | 9.3 mm |
| A(mm) | 1.38 mm | 1.38 mm | 1.38 mm | 1.38 mm | 1.38 mm |
| Nozzle diameter(µm) | 820 µm | 630 µm | 410 µm | 280 µm | 100 µm |
| B(mm) | 190 µm | 160 µm | 90 µm | 70 µm | 30 µm |
| Reduction ratio(%) | 86.2 | 88.4 | 93.5 | 94.9 | 97.8 |
| Size reduction(=B/A × 100) (%) | 13.8 | 11.6 | 6.5 | 5.1 | 2.2 |

[Embodiment 5] Manufacturing of Artificial Blood Vessel Having Lumen Structure 3 w/v % of sodium alginate was injected into the second head like the third embodiment, 3% gelatin which is temperature-sensitive hydrogel was injected into previously injected alginate by the printing method using the long nozzle. When prepared complex hydrogel was printed to calcium chloride of 200 Mn, it was induced that only alginate became gel but gelatin did not become gel. When the printed structure was put in liquid of 37° C., the alginate gel maintained the shape as it was, but gelatin was melted down to form the lumen structure.

[Embodiment 8] Manufacturing Blood Vessel Having Cells and Multiple Lumen Structure In the same way as the seventh embodiment, 3 w/v % of sodium alginate was injected into the second head like the seventh embodiment, 3% alginate in which smooth muscle cells were contained at concentration of more than 1×10$^7$ Cells/mL was injected into the 3% alginate using the 3D printer having the long nozzle, 3% gelatin in which vascular endothelial cells were contained at concentration of more than 1×10$^7$ Cells/mL was injected into alginate in which smooth muscle cells were contained. Through such continuous method, a blood vessel structure was copied.

Especially, aorta or vena cava of the blood vessel are laid one upon another in a quadruple cylindrical structure. Through such a method, a blood vessel of the quadruple structure can be printed easily, and the size can be adjusted (See the copy result of the quadruple cylindrical structure using A, B, C and D of FIG. 27), and a double structure of venula or a single structure of a micro-vessel can be copied in the same way.

While the present invention has been particularly shown and described with reference to exemplary embodiments thereof, it will be understood by those of ordinary skill in the art that various changes and modifications may be made therein without departing from the spirit and scope of the present invention.

INDUSTRIAL APPLICABILITY

The present invention relates to a three-dimensional (3D) printing system for manufacturing an artificial blood vessel and a method for manufacturing an artificial blood vessel using the same, wherein a cylindrical support having a hollow 3D porous structure including a thermoplastic polymer is manufactured and vertically fixed, and hydrogel divided into at least two sections is discharged into the support, thereby maintaining the structure and shape constantly even after printing and manufacturing an artificial blood vessel having a multilayered hollow structure. The present invention can manufacture an artificial blood vessel of a hollow form with a multilayer structure, and evenly maintain the structure and form of the artificial blood vessel even after printing. Therefore, the present invention has industrial applicability.

The invention claimed is:

1. A 3D printing system for manufacturing an artificial blood vessel comprising:
 a support manufacturing unit which is rotatable and forms a hollow cylindrical support of a 3D porous structure when polymer is discharged to an outer circumferential surface through a first head;
 the first head forming the hollow cylindrical support of the 3D porous structure by discharging the polymer to the support manufacturing unit;
 a holder for vertically holding and fixing the hollow cylindrical support manufactured through the first head; and
 a second head for discharging hydrogel, which is divided into at least two sections, into the hollow cylindrical support vertically held and fixed on the holder.

2. The 3D printing system according to claim 1, wherein the first head comprises: a first pneumatic cylinder ascending and descending to discharge the polymer; a first discharge unit for discharging the polymer by lowering of the first pneumatic cylinder; and a temperature control unit for controlling temperature of the discharged polymer.

3. The 3D printing system according to claim 1, wherein the second head comprises: a second pneumatic cylinder ascending and descending to discharge the hydrogel; a second discharge unit for discharging the hydrogel divided into at least two sections by lowering of the second pneumatic cylinder; and a temperature control unit for controlling temperature of the discharged hydrogel divided into at least two sections.

4. The 3D printing system according to claim 1, wherein the support manufacturing unit comprises: a rotary shaft which is rotatable when the polymer is discharged; a motor connected to one side of the rotary shaft to rotate the rotary shaft; and a bearing connected to another side of the rotary shaft to support the rotary shaft.

5. The 3D printing system according to claim 1, wherein the holder is movable in a vertical direction while the second head discharges the hydrogel divided into at least two sections.

6. The 3D printing system according to claim 1, wherein the polymer is thermoplastic polymer.

7. The 3D printing system according to claim 6, wherein the thermoplastic polymer comprises at least one of lactide, caprolactone, glycolide, dioxanone, propylene, ethylene, vinylchloride, butadiene, methyl methacrylate, acrylic acid, 2-hydroxyethylmethacrylate, carbonate, polyethylene terephalate, and combinations thereof.

8. The 3D printing system according to claim 1, wherein the hydrogel divided into at least two sections contains at least one of polymer gels, cells, growth factors, extracellular matrix, and combinations thereof, and a cross section of the hydrogel divided into the at least two sections discharged into the hollow cylindrical support and a cross section of the hydrogel divided into the at least two sections charged in a second pneumatic cylinder have a same pattern.

* * * * *